United States Patent [19]

Törnell

[11] Patent Number: 5,716,817
[45] Date of Patent: Feb. 10, 1998

[54] TRANSGENIC NON-HUMAN MAMMALS THAT EXPRESS HUMAN BSSL/CEL

[75] Inventor: Jan Birger Fredrik Törnell, Västra Frölunda, Sweden

[73] Assignee: Astra Aktiebolag, Sodertalje, Sweden

[21] Appl. No.: 442,806

[22] Filed: May 17, 1995

Related U.S. Application Data

[62] Division of Ser. No. 68,945, May 27, 1993, Pat. No. 5,616,483.

[30] Foreign Application Priority Data

| Jun. 11, 1992 | [SE] | Sweden | 9201809 |
| Jun. 12, 1992 | [SE] | Sweden | 9201826 |
| Jul. 3, 1992 | [SE] | Sweden | 9202088 |
| Mar. 19, 1993 | [SE] | Sweden | 9300902 |

[51] Int. Cl.$^6$ .................. C12N 15/00; C12N 15/09
[52] U.S. Cl. .................. 435/172.3; 435/69.1; 800/2; 935/52
[58] Field of Search .................. 800/2; 435/172.3, 435/69.1

[56] References Cited

U.S. PATENT DOCUMENTS

| 3,256,150 | 6/1966 | Nelson et al. | 424/94.6 |
| 4,079,125 | 3/1978 | Sipos | 424/94.6 |
| 4,873,316 | 10/1989 | Meade et al. | 530/412 |
| 4,944,944 | 7/1990 | Tang et al. | 424/94.6 |
| 5,173,408 | 12/1992 | Lange et al. | 435/69.1 |
| 5,200,183 | 4/1993 | Tang et al. | 424/94.6 |

FOREIGN PATENT DOCUMENTS

| 9115234 | 10/1991 | WIPO . |
| 9118923 | 12/1991 | WIPO . |

OTHER PUBLICATIONS

Nilsson et al. "cDNA cloning of human-milk bile-salt-stimulated lipase and evidence for its identity to pancreatic carboxylic ester hydrolase." Eur. J. Biochem. 192: 543–550, 1990.

Baba et al. "Structure of the human milk bile salt activated lipase." Biochemistry 30: 500–510, 1991.

Kyger et al. "Cloning of the bovine pancreatic cholesterol esterase/lysophospholipase". Biochem. Biophys. Res. Comm. 164: 1302–1309, 1989.

Hui, D.Y. and Kissel, J.A. "Sequence identity between human pancreatic cholesterol esterase and bile salt–stimulated milk lipase." FEBS 276: 131–134, 1990.

DiPersio et al. "Identification of the active site serine in pancreatic cholesterol esterase by chemical modification and site–specific mutagenesis." J. Biol. Chem. 265: 16, 801–16, 806, 1990.

Han et al. "Isolation of full–length putative rat lysohospholipase cDNA using improved methods for mRNA isolation and cDNA cloning". Biochemistry 26: 1617–1625, 1987.

Wang, et al., Biochim. Biophys. Acta 1166:1–19 (1993).

Whitelaw, et al., Transgenic Res. 1:3–13 (1991).

Hennighausen, et al., Curr. Opinion Biotechnical. 1:74–78 (1990).

DiPersio, et al., Protein Expression and Purification 3:114–120 (1992).

Hennighausen et al. 1990. Protein Expression and Purification, 1:3–8.

Fontaine et al. 1991. Biochemistry 30:7008–7014.

Primary Examiner—Brian R. Stanton
Attorney, Agent, or Firm—White & Case

[57] ABSTRACT

The present invention relates to a DNA molecule containing intron sequences and encoding a human protein which is, depending on the site of action, called Bile Salt-Stimulated Lipase (BSSL) or Carboxyl Ester Lipase (CEL). The DNA molecule is advantageously used in the production of recombinant human BSSL/CEL, preferably by means of production in transgenic non-human mammals. The recombinant human BSSL/CEL can be used as a constituent of infant formulas used for feeding infants as a substitute for human milk, or in the manufacture of medicaments against e.g. fat malabsorption, cystic fibrosis and chronic pancreatitis.

4 Claims, 12 Drawing Sheets

Fig.4A.

```
-1640  GGATCCCTCG AACCAGGAG TTCAAGACTG CAGTGAGCTA TGATTGTGCC ACTGCACTCT AGCCTGGGTG ACAGAGACCC TGTCTCAAAA AAACAAACAA

-1540  ACAAAAAACC TCTGTGGACT CCGGGGTGATA ATGACATGTC AATGTGGATT CATCAGGTGT TAACAGCTGT ACCCCCTGGT GGGGATGTGT GATAACGGGG

-1440  GAGACTGGAG TGGGGCGAGG ACATACGGGA AATCTCTGTA ATCTTCCTCT AATTTTGCTG TGAACCTAAA GCTGCTCTAA AAATGTACAT AGATATAAAC

-1340  TGGGGCCTTC CTTTCCCTCT GCCCTGCCCC AGCCCTCCCC CACCCCCTTC TGCCTCCCCT CTGCCCCTCC CTTTCCTCCT TAGCCACTGT
                                                                                                     ——— 5D ———

-1240  AAATGACACT GCAGCAAAGG TCTGAGGCAA ATGCCTTTGC CCTGGGGGGC CCCAGCCACC TGCAGGCCCC TTATTTCCTG TGGCCCGAGCT CCTCCTCCCA
       ——— 5C ———                                                   ——— 4B ———

-1140  CCCTCCAGTC CTTTCCCCAG CCTCCTCCGC CCACTAGGCC CCTGAATTG CTGGCACCGG CTGTGGTCGA CAGACAGAGG GACAGACGTG GCTCTGCAGG

-1040  TCCACTCGGT CCCTGGCACC GGCCGCAGGG CTGGCAGAAC GGGAGTGTGG TTGGTGTGGG AAGCACAGGC CCCAGTGTCT CCTGGGGGAC TGTTGGGTGG

-940   GAAGGCTCTG GCTGCCCTCA CCCTGTTCCC ATCACTGCAG AGGGCTGTGC GGTGGCTGGA GCTGCCACTG AGTGTCTCGG TGAGGGTGAC CTTCACACTGG
                                                      ——— 1B ———                                    ——— 2 ———

-840   CTGAGCTTAA AGGCCCCATC TGAAGACTTT GTTCGTGGTG TTCTTTCACT TCTTCAGAGCC TTTCCTGGCT CCAGGATTAA TACCTGTTCA CAGAAAATAC
```

Fig. 4B.

```
                   ————— 5B —————
-740  GAGTGGCCTC CTCCTCCACA ACCTTCTCCC TTCCCTCCCT CTGGCCTCTT TCCCTCCCCG CTGGCCTCTT TCCCTCCCCT TCTGTCACTC TGCCTGGGCA TGCCCCAGGG

-640  CCTCGGCTGG GCCCTTTGTT TCCACAGGGA AACCTTACACG GTTGGGCTAG ATGCCTCCCGC ACCCCCCCAC CCACACCCCC TGAGCCTCTA GTCCTCCCTC

-540  CCAGGACACA TCAGGCTGGA TGGTGACACT TCCACACCCT TGAGTGGGAC TGCCTTGTGC TGCTCTGGGA TTCGCACCCA GCTTGGACTA CCCGCTCCAC

-440  GGGCCCCAGG AAAAGCTCGT ACAGATAAGG TCAGCCACAC GAGTGGAGGG CCTGCAGCAT GCTGCCCTTT CTGTCCAGA AGTCACGTGC TCGGTCCCCT
                                                                                        ————— 4A —————

-340  CTGAAGCCCC TTTGGGGGACC TAGGGGACAA GCAGGGGCATG GAGACATGGA GACAAAGTAT GCCCTTTTCT CTGACAGTGA CACCAAGCCC TGTGAACAAA

-240  CCAGAAGGCA GGGGACTGTG CACCCTGCCC GGCCCCACCA TCCCCCTTAC CACCCGCCAC CTTGCCACCT GCCCTCTGCTC CCAGGTAAGT GGTAACCTGC
                          ————— 1A —————

-140  ACAGGTGCAC TGTGGGTTTG GGGAAAACTG GATCTCCCTG CACCTGAGGG GGTAGAGGGG AGGGAGTGCC TGAGAGCTCA TGAACAAGCA TGTGACCTTG

-40   GATCCAGCTC CATAAATACC CGAGGCCCAG GGGGAGGGCC ........
```

Fig.9A.
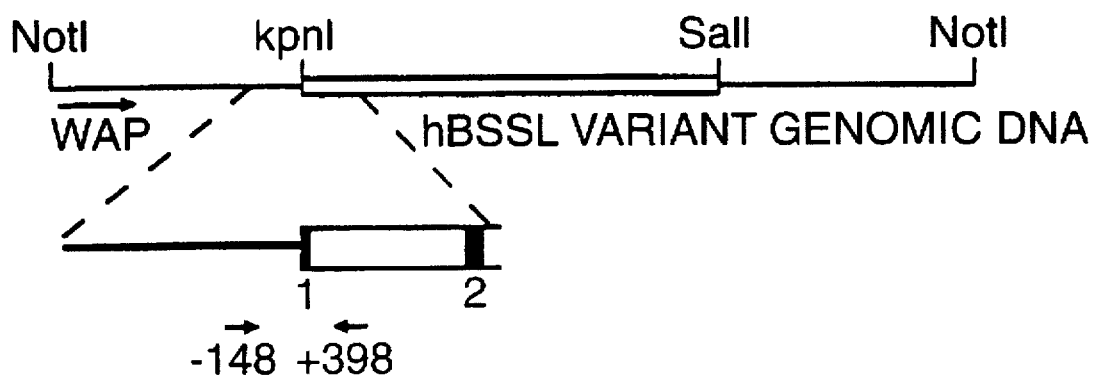
Fig.9B.
| Primer | Sequence (5'-3') |
|---|---|
| 5'-prime | CTGTGTGGCAAGAAGGAAGTGTTGT |
| 3'-prime | CAACTCCTGACCTCAAGTGATC |
Fig.9C.
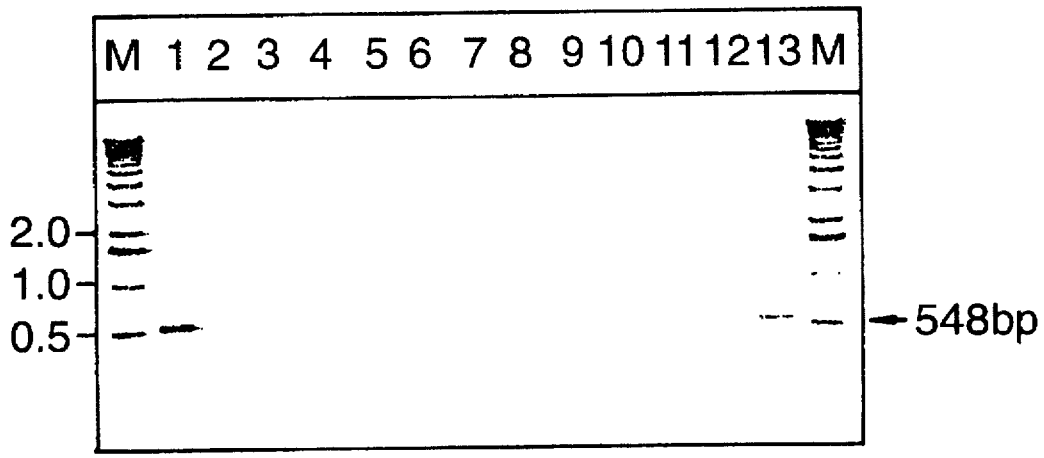

SEQUENCE LISTING ( 1 ) GENERAL INFORMATION:

( i i i ) NUMBER OF SEQUENCES: 58

( 2 ) INFORMATION FOR SEQ ID NO:1:

( i ) SEQUENCE CHARACTERISTICS:
        ( A ) LENGTH: 11531 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Homo sapiens
        ( F ) TISSUE TYPE: Mammary gland ( i x ) FEATURE:
        ( A ) NAME/KEY: CDS
        ( B ) LOCATION: join(1653..1727, 4071..4221, 4307..4429, 4707
            . . 4904, 6193..6323, 6501..6608, 6751..6868, 8335
            . . 8521, 8719..8922, 10124..10321, 10650..11394)

( i x ) FEATURE:
        ( A ) NAME/KEY: mat_peptide
        ( B ) LOCATION: join(1722..1727, 4071..4221, 4307..4429, 4707
            . . 4904, 6193..6323, 6501..6608, 6751..6868, 8335
            . . 8521, 8719..8922, 10124..10321, 10650..11391)
        ( D ) OTHER INFORMATION: /EC_number=3.1.1.1
            / product="Bile Salt-Stimulated Lipase"

( i x ) FEATURE:
        ( A ) NAME/KEY: 5'UTR
        ( B ) LOCATION: 1..1640

( i x ) FEATURE:
        ( A ) NAME/KEY: TATA_signal
        ( B ) LOCATION: 1611..1617

( i x ) FEATURE:
        ( A ) NAME/KEY: exon
        ( B ) LOCATION: 1641..1727

( i x ) FEATURE:
        ( A ) NAME/KEY: exon
        ( B ) LOCATION: 4071..4221

( i x ) FEATURE:
        ( A ) NAME/KEY: exon ( B ) LOCATION: 4307..4429

( i x ) FEATURE:
              ( A ) NAME/KEY: exon
              ( B ) LOCATION: 4707..4904

( i x ) FEATURE:
              ( A ) NAME/KEY: exon
              ( B ) LOCATION: 6193..6323

( i x ) FEATURE:
              ( A ) NAME/KEY: exon
              ( B ) LOCATION: 6501..6608

( i x ) FEATURE:
              ( A ) NAME/KEY: exon
              ( B ) LOCATION: 6751..6868

( i x ) FEATURE:
              ( A ) NAME/KEY: exon
              ( B ) LOCATION: 8335..8521

( i x ) FEATURE:
              ( A ) NAME/KEY: exon
              ( B ) LOCATION: 8719..8922

( i x ) FEATURE:
              ( A ) NAME/KEY: exon
              ( B ) LOCATION: 10124..10321

( i x ) FEATURE:
              ( A ) NAME/KEY: exon
              ( B ) LOCATION: 10650..11490

( i x ) FEATURE:
              ( A ) NAME/KEY: 3'UTR
              ( B ) LOCATION: 11491..11531

( x i ) SEQUENCE DESCRIPTION: SEQ ID NO:1:

| | | | | | | |
|---|---|---|---|---|---|---|
| GGATCCCTCG | AACCCAGGAG | TTCAAGACTG | CAGTGAGCTA | TGATTGTGCC | ACTGCACTCT | 60 |
| AGCCTGGGTG | ACAGAGACCC | TGTCTCAAAA | AACAAACAA | ACAAAAAACC | TCTGTGGACT | 120 |
| CCGGGTGATA | ATGACATGTC | AATGTGGATT | CATCAGGTGT | TAACAGCTGT | ACCCCCTGGT | 180 |
| GGGGATGTT | GATAACGGGG | GAGACTGGAG | TGGGCGAGG | ACATACGGGA | AATCTCTGTA | 240 |
| ATCTTCCTCT | AATTTTGCTG | TGAACCTAAA | GCTGCTCTAA | AAATGTACAT | AGATATAAAC | 300 |
| TGGGGCCTTC | CTTTCCCTCT | GCCCTGCCCC | AGCCCTCCCC | CACCTCCTTC | CTCTCCCTGC | 360 |
| TGCCTCCCCT | CTGCCCTCCC | CTTTCCTCCT | TAGCCACTGT | AAATGACACT | GCAGCAAAGG | 420 |
| TCTGAGGCAA | ATGCCTTTGC | CCTGGGCGC | CCAGCCACC | TGCAGGCCCC | TTATTTCCTG | 480 |
| TGGCCGAGCT | CCTCCTCCCA | CCCTCCAGTC | CTTTCCCCAG | CCTCCCTCGC | CCACTAGGCC | 540 |
| TCCTGAATTG | CTGGCACCGG | CTGTGGTCGA | CAGACAGAGG | GACAGACGTG | GCTCTGCAGG | 600 |
| TCCACTCGGT | CCCTGGCACC | GGCCGCAGGG | GTGGCAGAAC | GGGAGTGTGG | TTGGTGTGGG | 660 |
| AAGCACAGGC | CCCAGTGTCT | CCTGGGGGAC | TGTTGGGTGG | GAAGGCTCTG | GCTGCCCTCA | 720 |
| CCCTGTTCCC | ATCACTGCAG | AGGGCTGTGC | GGTGGCTGGA | GCTGCCACTG | AGTGTCTCGG | 780 |
| TGAGGGTGAC | CTCACACTGG | CTGAGCTTAA | AGGCCCCATC | TGAAGACTTT | GTTCGTGGTG | 840 |
| TTCTTTCACT | TCTCAGAGCC | TTTCCTGGCT | CCAGGATTAA | TACCTGTTCA | CAGAAAATAC | 900 |
| GAGTCGCCTC | CTCCTCCACA | ACCTCACACG | ACCTTCTCCC | TTCCCTCCCG | CTGGCCTCTT | 960 |
| TCCCTCCCCT | TCTGTCACTC | TGCCTGGGCA | TGCCCCAGGG | CCTCGGCTGG | GCCCTTTGTT | 1020 |
| TCCACAGGGA | AACCTACATG | GTTGGGCTAG | ATGCCTCCGC | ACCCCCCAC | CCACACCCCC | 1080 |
| TGAGCCTCTA | GTCCTCCCTC | CAGGACACA | TCAGGCTGGA | TGGTGACACT | TCCACACCCT | 1140 |
| TGAGTGGGAC | TGCCTTGTGC | TGCTCTGGGA | TTCGCACCCA | GCTTGGACTA | CCCGCTCCAC | 1200 |

| | | | | | |
|---|---|---|---|---|---|
| GGGCCCCAGG | AAAAGCTCGT | ACAGATAAGG | TCAGCCACAT | GAGTGGAGGG | CCTGCAGCAT | 1260 |
| GCTGCCCTTT | CTGTCCCAGA | AGTCACGTGC | TCGGTCCCCT | CTGAAGCCCC | TTTGGGGACC | 1320 |
| TAGGGGACAA | GCAGGGCATG | GAGACATGGA | GACAAAGTAT | GCCCTTTTCT | CTGACAGTGA | 1380 |
| CACCAAGCCC | TGTGAACAAA | CCAGAAGGCA | GGGCACTGTG | CACCCTGCCC | GGCCCCACCA | 1440 |
| TCCCCCTTAC | CACCCGCCAC | CTTGCCACCT | GCCTCTGCTC | CCAGGTAAGT | GGTAACCTGC | 1500 |
| ACAGGTGCAC | TGTGGGTTTG | GGGAAAACTG | GATCTCCCTG | CACCTGAGGG | GGTAGAGGGG | 1560 |
| AGGGAGTGCC | TGAGAGCTCA | TGAACAAGCA | TGTGACCTTG | GATCCAGCTC | CATAAATACC | 1620 |
| CGAGGCCCAG | GGGGAGGGCC | ACCCAGAGGC | TG ATG CTC | ACC ATG GGG | CGC CTG | 1673 |
| | | | Met Leu | Thr Met Gly | Arg Leu | |
| | | | -23 | -20 | | |

| | | | | | |
|---|---|---|---|---|---|
| CAA CTG GTT GTG TTG GGC CTC ACC TGC TGC TGG GCA GTG GCG AGT GCC | | | | | | 1721 |
| Gln Leu Val Val Leu Gly Leu Thr Cys Cys Trp Ala Val Ala Ser Ala | | | | | | |
| -15 | | -10 | | -5 | | |

| | | | | | |
|---|---|---|---|---|---|
| GCG AAG | GTAAGAGCCC | AGCAGAGGGG | CAGGTCCTGC | TGCTCTCTCG | CTCAATCAGA | 1777 |
| Ala Lys | | | | | | |
| 1 | | | | | | |

| | | | | | |
|---|---|---|---|---|---|
| TCTGGAAACT | TCGGGCCAGG | CTGAGAAAGA | GCCCAGCACA | GCCCGCAGC | AGATCCCGGG | 1837 |
| CACTCACGCT | CATTTCTATG | GGGACAGGTG | CCAGGTAGAA | CACAGGATGC | CCAATTCCAT | 1897 |
| TTGAATTTCA | GATAAACTGC | CAAGAACTGC | TGTGTAAGTA | TGTCCCATGC | AATATTTGAA | 1957 |
| ACAAATTTCT | ATGGGCCGGG | CGCAGTGGCT | CACACCTGCA | ATCCCACCAG | TTTGGGAGGC | 2017 |
| CGAGGTGGGT | GGATCACTTG | AGGTCAGGAG | TTGGAGACCA | GCCTGGCCAA | CATGGTGAAA | 2077 |
| CCCCGTCTCT | ACTAAAAATA | CAAATATTAA | TCGGGCGTGG | TGGTGGGTGC | CTGTAATCCC | 2137 |
| AGCTACTCGG | GAGGCTGAGG | CAGGAGAACC | GCTTGAAGCT | GGGAGGTGGA | GATTGCGGTG | 2197 |
| AGCTGAGATC | ACGCTACTGC | ACTCCAGCCT | GGGTGACAGG | GCGAGACTCT | GTCTCAAAAA | 2257 |
| ATAGAAAAAG | AAAAAAATGA | ACATACTAA | AAACAATTC | ACTGTTTACC | TGAAATTCAA | 2317 |
| ATGTAACTGG | GCCTCTTGAA | TTTACATTTG | CTAATCCTGG | TGATTCCACC | TACCAACCTC | 2377 |
| TCTGTTGTTC | CCATTTTACA | GAAGGGGAAA | CGGGCCCAGG | GGCAGGGAGT | GTGGAGAGCA | 2437 |
| GGCAGACGGG | TGGAGAGAAG | CAGGCAGGCA | GTTTGCCCAG | CATGGCACAG | CTGCTGCCTC | 2497 |
| CTATTCCTGT | GCAGGAAGCT | GAAAGCCGGG | CTACTCCACA | CCCGGGTCCG | GGTCCCTCCA | 2557 |
| GAAAGAGAGC | CGGCAGGCAG | GAGCTCTCTC | GAGGCATCCA | TAAATTCTAC | CCTCTCTGCC | 2617 |
| TGTGAAGGAG | AAGCCACAGA | AACCCCAAGC | CCCACAGGAA | GCCGGTGTCG | GTGCCCGGCC | 2677 |
| CAGTCCCTGC | CCCCAGCAGG | AGTCACACAG | GGACCCCAG | ATCCCAACCA | CGCTGTTCTG | 2737 |
| CTGCCTGCGG | TGTCTCAGGC | CCTGGGGACT | CCTGTCTCCA | CCTCTGCTGC | CTGCTCTCCA | 2797 |
| CACTCCCTGG | CCCTGGGACC | GGGAGGTTTG | GGCAGTGGTC | TTGGGCTCCT | GACTCAAAGG | 2857 |
| AGAGGTCACC | TTCTTCTTGG | GCGAGCTCTT | CTTGGGGTGC | TGAGAGGCCT | TCGGCAGGTC | 2917 |
| ATCACGACCC | CTCCCCATTT | CCCACCCTG | AGGCCCTCTG | GCCAGTCTCA | ATTGCACAGG | 2977 |
| GATCACGCCA | CTGGCACAAG | GAGACACAGA | TGCCTCGCAG | GGGATGCCCA | CGATGCCTGC | 3037 |
| ATGTGTTGCT | TCTGGTTCCT | TTCCTCCAGT | TCCAACCGCC | GCACTCTCCC | ACACCAGTGT | 3097 |
| GACAGGGGC | CCATCACCCT | AGACTTCAGA | GGGCTGCTGG | GACCCTGGCT | GGGCCTGGGG | 3157 |
| GTGTAGGGCC | ACCCTGCCCT | TCCCCACCTG | GAACCTGGCA | CAGGTGACAG | CCAGCAAGCA | 3217 |
| ATGACCTGGT | CCCACCATGC | ACCACGGGAA | GAGGGAGCTG | CTGCCCAAGA | TGGACAGGAG | 3277 |
| GTGGCACTGG | GGCAGACAGC | TGCTTCTCAA | CAGGGTGACT | TCAAGCCCAA | AAGCTGCCCA | 3337 |
| GCCTCAGTTC | CGTCAGGGAC | AGAGGGTGGA | TGAGCACCAA | CCTCCAGGCC | CCTCGTGGGG | 3397 |

| | | | | | |
|---|---|---|---|---|---|
| GTGGACAGCT | TGGTGCACAG | AGGCCATTTT | CATGGCACAG | GGAAGCGTGG | CGGGGGTGGG | 3457 |
| AGGTGTGGTC | CCTAGGGGGT | TCTTTACCAG | CAGGGGGCTC | AGGAACTGTG | GGACTTGGG | 3517 |
| CATGGGGCCA | TCGACTTTGT | GCCCAGCCAG | CTAGGCCCTG | TGCAGGGAGA | TGGGAGGAGG | 3577 |
| GAAAAGCAGG | CCCCACCCCT | CAGAAAGGAG | GAAGGTTGGT | GTGAAACATC | CCGGGTACAC | 3637 |
| TGAGCATTGG | GTACACTCCT | CCCGGGAGCT | GGACAGGCCT | CCATGTGAT | GGCAAACAGG | 3697 |
| CCGACAGGAG | ACACGGCTGT | TGCTCGTCTT | CCACATGGGG | AAACTGAGGA | TCGGAGTCAA | 3757 |
| AGCTGGGCGG | CCATAGCCAG | AACCCAAACC | TCCATCCCAC | CTCTTGGCCG | GCTTCCCTAG | 3817 |
| TGGAACACT | GGTTGAACCA | GTTTCCTCTA | AGATTCTGGG | AGCAGGACAC | CCCCAGGGAT | 3877 |
| AAGGAGAGGA | ACAGGAATCC | TAAAGCCCTG | AGCATTGCAG | GGCAGGGGT | GCTGCCTGGG | 3937 |
| TCTCCTGTGC | AGAGCTGTCC | TGCTTTGAAG | CTGTCTTTGC | CTCTGGGCAC | GCGGAGTCGG | 3997 |
| CTTGCCTTGC | CCCCTCCGGA | TTCAGGCCGA | TGGGGCTTGA | GCCCCCTGA | CCCTGCCCGT | 4057 |

```
GTCTCCCTCG CAG CTG GGC GCC GTG TAC ACA GAA GGT GGG TTC GTG GAA          4106
        Leu Gly Ala Val Tyr Thr Glu Gly Gly Phe Val Glu
              5                     10

GGC GTC AAT AAG AAG CTC GGC CTC CTG GGT GAC TCT GTG GAC ATC TTC         4154
Gly Val Asn Lys Lys Leu Gly Leu Leu Gly Asp Ser Val Asp Ile Phe
 15              20              25              30

AAG GGC ATC CCC TTC GCA GCT CCC ACC AAG GCC CTG GAA AAT CCT CAG         4202
Lys Gly Ile Pro Phe Ala Ala Pro Thr Lys Ala Leu Glu Asn Pro Gln
         35              40              45

CCA CAT CCT GGC TGG CAA  G GTGGGAGTGG GTGGTGCCGG ACTGGCCCTG             4251
Pro His Pro Gly Trp Gln
         50

CGGCGGGGCG GGTGAGGGCG GCTGCCTTCC TCATGCCAAC TCCTGCCACC TGCAG  GG        4308
                                                            Gly

ACC CTG AAG GCC AAG AAC TTC AAG AAG AGA TGC CTG CAG GCC ACC ATC         4356
Thr Leu Lys Ala Lys Asn Phe Lys Lys Arg Cys Leu Gln Ala Thr Ile
         55              60              65

ACC CAG GAC AGC ACC TAC GGG GAT GAA GAC TGC CTG TAC CTC AAC ATT         4404
Thr Gln Asp Ser Thr Tyr Gly Asp Glu Asp Cys Leu Tyr Leu Asn Ile
 70              75              80              85

TGG GTG CCC CAG GGC AGG AAG CAA  G GTCTGCCTCC CCTCTACTCC                4449
Trp Val Pro Gln Gly Arg Lys Gln
             90

CCAAGGGACC CTCCCATGCA GCCACTGCCC CGGGTCTACT CCTGGCTTGA GTCTGGGGGC       4509
TGCAAAGCTG AACTTCCATG AAATCCACA GAGGCGGGGA GGGGAGCGCC CACTGCCGTT        4569
GCCCAGCCTG GGGCAGGGCA GCGCCTTGGA GCACCTCCCT GTCTTGGCCC CAGGCACCTG       4629
CTGCACAGGG ACAGGGGACC GGCTGGAGAC AGGGCCAGGC GGGGCGTCTG GGTCACCAG        4689
CCGCTCCCCC ATCTCAG  TC TCC CGG GAC CTG CCC GTT ATG ATC TGG ATC         4738
                  Val Ser Arg Asp Leu Pro Val Met Ile Trp Ile
                           95              100

TAT GGA GGC GCC TTC CTC ATG GGG TCC GGC CAT GGG GCC AAC TTC CTC         4786
Tyr Gly Gly Ala Phe Leu Met Gly Ser Gly His Gly Ala Asn Phe Leu
105              110             115             120

AAC AAC TAC CTG TAT GAC GGC GAG GAG ATC GCC ACA CGC GGA AAC GTC         4834
Asn Asn Tyr Leu Tyr Asp Gly Glu Glu Ile Ala Thr Arg Gly Asn Val
         125             130             135

ATC GTG GTC ACC TTC AAC TAC CGT GTC GGC CCC CTT GGG TTC CTC AGC         4882
Ile Val Val Thr Phe Asn Tyr Arg Val Gly Pro Leu Gly Phe Leu Ser
         140             145             150

ACT GGG GAC GCC AAT CTG CCA  G GTGCGTGGGT GCCTTCGGCC CTGAGGTGGG         4934
Thr Gly Asp Ala Asn Leu Pro
         155
```

```
GCGACCAGCA TGCTGAGCCC AGCAGGGAGA TTTTCCTCAG CACCCCTCAC CCCAAACAAC     4994
CAGTGGCGGT TCACAGAAAG ACCCGGAAGC TGGAGTAGAA TCATGAGATG CAGGAGGCCC     5054
TTGGTAGCTG TAGTAAAATA AAAGATGCTG CAGAGGCCGG GAGAGATGGC TCACGCCTGT     5114
AATCCCAGCA CTTTAGGAGG CCCACACAGG TGGGTCACTT GAGCGCAGAA GTTCAAGACC     5174
AGCCTGAAAA TCACTGGGAG ACCCCCATCT CTACACAAAA ATTAAAAATT AGCTGGGGAC     5234
TGGGCGCGGC GGCTCACCTC TGTAATCCCA GCACGTTGGG AGCCCAAGGT GGGTAGATCA     5294
CCTGAGGTCA GGAGTTTGAG ACCAGCCTGA CTAAAATGGA GAAACCTCTT CTCTACTAAA     5354
AATACAAAAT TAGCCAGGCG TGGTGGCGCT TGCCTGTAAT CCCAGCTACT CGGGAGGCTG     5414
AGGCAGGAGA ATCGCTTGAA CTCAGGAGGC GGAGGTTGCG GTGAGCCGAG ATCATGCCAC     5474
TGCACTCCAG CCTGGAGAAC AAGAGTAAAA CTCTGTCTCA AAAAAAAAA AAAAAAAAA      5534
ATAGCCAGGC GTGGTATCTC ATGCCTCTGT CCTCAGCTAC CTGGGAGGCA GAGGTGGAAG     5594
GATCGCTTGA GCCCAGGGGT TCAAAGCTGC AGTGAGCCGT GGTCGTGCCA CTGCACTCCA     5654
GCCTGGGCGA CAGAGTGAGG CCCCATCTCA AAAATAAGAG GCTGTGGGAC AGACAGACAG     5714
GCAGACAGGC TGAGGCTCAG AGAGAAACCA GGAGAGCAGA GCTGAGTGAG AGACAGAGAA     5774
CAATACCTTG AGGCAGAGAC AGCTGTGGAC ACAGAAGTGG CAGGACACAG ACAGGAGGGA     5834
CTGGGGCAGG GGCAGGAGAG GTGCATGGGC CTGACCATCC TGCCCCGAC  AAACACCACC     5894
CCCTCCAGCA CCACACCAAC CCAACCTCCT GGGGACCCAC CCCATACAGC ACCGCACCCG     5954
ACTCAGCCTC CTGGGACCCA CCCACTCCAG CAACCAACGT GACCTAGTCT CCTGGGACCC     6014
ACCCCCTCCA GCACCCTACC CGACCCAGCT TCTTAGGGAC CCACCATTTG CCAACTGGGC     6074
TCTGCCATGG CCCCAACTCT GTTGAGGGCA TTTCCACCCC ACCTATGCTG ATCTCCCCTC     6134
CTGGAGGCCA GGCCTGGGCC ACTGGTCTCT AGCACCCCCT CCCCTGCCCT GCCCCCAG GT  6194
                                                              Gly
                                                              160

AAC TAT GGC CTT CGG GAT CAG CAC ATG GCC ATT GCT TGG GTG AAG AGG    6242
Asn Tyr Gly Leu Arg Asp Gln His Met Ala Ile Ala Trp Val Lys Arg
            165                 170                 175

AAT ATC GCG GCC TTC GGG GGG GAC CCC AAC AAC ATC ACG CTC TTC GGG    6290
Asn Ile Ala Ala Phe Gly Gly Asp Pro Asn Asn Ile Thr Leu Phe Gly
        180                 185                 190

GAG TCT GCT GGA GGT GCC AGC GTC TCT CTG CAG GTCTCGGGAT CCCTGTGGGG  6343
Glu Ser Ala Gly Gly Ala Ser Val Ser Leu Gln
        195                 200

AGGGCCTGCC CCACAGGTTG AGAGGAAGCT CAAACGGGAA GGGGAGGGTG GGAGGAGGAG    6403
CGTGGAGCTG GGGCTGTGGT GCTGGGGTGT CCTTGTCCCA GCGTGGGGTG GGCAGAGTGG    6463
GGAGCGGCCT TGGTGACGGG ATTTCTGGGT CCCGTAG ACC CTC TCC CCC TAC AAC    6518
                                        Thr Leu Ser Pro Tyr Asn
                                                    205

AAG GGC CTC ATC CGG CGA GCC ATC AGC CAG AGC GGC GTG GCC CTG AGT    6566
Lys Gly Leu Ile Arg Arg Ala Ile Ser Gln Ser Gly Val Ala Leu Ser
    210                 215                 220                 225

CCC TGG GTC ATC CAG AAA AAC CCA CTC TTC TGG GCC AAA AAG          6608
Pro Trp Val Ile Gln Lys Asn Pro Leu Phe Trp Ala Lys Lys
                    230                 235

GTAAACGGAG GAGGGCAGGG CTGGGCGGGG TGGGGGCTGT CCACATTTCC GTTCTTTATC    6668
CTGGACCCCA TCCTTGCCTT CAAATGGTTC TGAGCCCTGA GCTCCGGCCT CACCTACCTG    6728
CTGGCCTTGG TTCTGCCCCC AG GTG GCT GAG AAG GTG GGT TGC CCT GTG GGT    6780
                       Val Ala Glu Lys Val Gly Cys Pro Val Gly
                                240                 245
```

-continued

| | | | | | | | | | | | | | | | |
|---|---|---|---|---|---|---|---|---|---|---|---|---|---|---|---|
| GAT | GCC | GCC | AGG | ATG | GCC | CAG | TGT | CTG | AAG | GTT | ACT | GAT | CCC | CGA | GCC | 6828 |
| Asp | Ala | Ala | Arg | Met | Ala | Gln | Cys | Leu | Lys | Val | Thr | Asp | Pro | Arg | Ala | |
| 250 | | | | 255 | | | | 260 | | | | | 265 | | |
| CTG | ACG | CTG | GCC | TAT | AAG | GTG | CCG | CTG | GCA | GGC | CTG | GAG | T GTGAGTAGCT | | 6878 |
| Leu | Thr | Leu | Ala | Tyr | Lys | Val | Pro | Leu | Ala | Gly | Leu | Glu | | | |
| | | | | 270 | | | | 275 | | | | | | | |

GCTCGGGTTG GCCCATGGGG TCTCGAGGTG GGGGTTGAGG GGGGTACTGC CAGGGAGTAC 6938
TCCGGAGGAG AGAGGAAGGT GCCAGAGCTG CGGTCTTGTC CTGTCACCAA CTAGCTGGTG 6998
TCTCCCCTCG AAGGCCCCAG CTGTAAGGGA GAGGGGGTGC CGTTCTTCT TTTTTTTGA 7058
GATGGAGTCT CACTGTTGCC CAGGCTGGAG TGCAGTGTCA CGATCTCAGC TCACTGCAAC 7118
CTCCACCTCC TGGGTTCAAG TGATTCTCTG ACTCAACCTC CATGTAGCT GGGACTACAG 7178
GCACATGCCA CCATGCCCAG ATAATTTTC TGTGTGTTTA GTAGGGATGG AGTTTCATCG 7238
TGTTAGCTAG GATGATCTCG GTCTTGGGAC CTCATGATCT GCCCACCTCG GCCTCCCAAA 7298
GTGCTGGAAT TACAGGCGTG AGCCACTGTG CCCGGCCCCT TCTTTATTCT TATCTCCCAT 7358
GAGTTACAGA CTCCCCTTTG AGAAGCTGAT GAACATTTGG GGCCCCCTCC CCCACCTCAT 7418
GCATTCATAT GCAGTCATTT GCATATAATT TTAGGGAGAC TCATAGACCT CAGACCAAGA 7478
GCCTTTGTGC TAGATGACCG TTCATTCATT CGTTCATTCA TTCAGCAAAC ATTTACTGAA 7538
CCGTAGCACT GGGGCCCAGC CTCCAGCTCC ACTATTCTGT ACCCGGGAA GGCCTGGGGA 7598
CCCATTCCAC AAACACCTCT GCATGTCAGC CTTACCAGCT TGCTACGCTA AGGCTGTCCC 7658
TCACTCATTC TTCTATGGCA ACATGCCATG AAGCCAAGTC ATCTGCACGT TTACCTGACA 7718
TGAGCTCAAC TGCACGGGCT GGACAAGCCC AAACAAAGCA ACCCCACGG CCCCGCTAGA 7778
AGCAAAACCT GCTGTGCTGG GCCCAGTGAC AGCCAGGCCC CGCCTGCCTC AGCAGCCACT 7838
GGGTCCTCTA GGGGCCCGTC CAGGGGTCTG GAGTACAATG CAGACCTCCC ACCATTTTG 7898
GCTGATGGAC TGGAACCCAG CCCTGAGAGA GGGAGCTCCT TCTCCATCAG TTCCCTCAGT 7958
GGCTTCTAAG TTTCCTCCTT CCTGCTTCAG GCCCAGCAAA GAGAGAGAGG AGAGGGAGGG 8018
GCTGCCGCTG AAGAGGACAG ATCTGGCCCT AGACAGTGAC TCTCAGCCTG GGACGTGTG 8078
GCAGGGCCTG GAGACATCTG TGATTGTCAC AGCTGGGGAG GGGGTGCTCC TGGCACCTCG 8138
TGGGTCGAGG CCGGGGATGC TCTAAACATC CTACAGGGCA CAGGATGCCC CTGATGGTGC 8198
AGAATCAACC CTGCCCCAAG TGTCCATAGA TCAGAGAAGG GAGGACATAG CCAATTCCAG 8258
CCCTGAGAGG CAAGGGGCGG CTCAGGGGAA ACTGGGAGGT ACAAGAACCT GCTAACCTGC 8318

| | | | | | | | | | | |
|---|---|---|---|---|---|---|---|---|---|---|
| TGGCTCTCCC ACCCAG | AC | CCC | ATG | CTG | CAC | TAT | GTG | GGC | TTC | GTC | CCT | 8366 |
| | | Tyr | Pro | Met | Leu | His | Tyr | Val | Gly | Phe | Val | Pro | |
| | | | | 280 | | | | | 285 | | | | |
| GTC | ATT | GAT | GGA | GAC | TTC | ATC | CCC | GCT | GAC | CCG | ATC | AAC | CTG | TAC | GCC | 8414 |
| Val | Ile | Asp | Gly | Asp | Phe | Ile | Pro | Ala | Asp | Pro | Ile | Asn | Leu | Tyr | Ala | |
| 290 | | | | | 295 | | | | 300 | | | | | 305 | | |
| AAC | GCC | GCC | GAC | ATC | GAC | TAT | ATA | GCA | GGC | ACC | AAC | AAC | ATG | GAC | GGC | 8462 |
| Asn | Ala | Ala | Asp | Ile | Asp | Tyr | Ile | Ala | Gly | Thr | Asn | Asn | Met | Asp | Gly | |
| | | | | 310 | | | | | 315 | | | | | 320 | | |
| CAC | ATC | TTC | GCC | AGC | ATC | GAC | ATG | CCT | GCC | ATC | AAC | AAG | GGC | AAC | AAG | 8510 |
| His | Ile | Phe | Ala | Ser | Ile | Asp | Met | Pro | Ala | Ile | Asn | Lys | Gly | Asn | Lys | |
| | | | 325 | | | | | 330 | | | | | 335 | | | |
| AAA | GTC | ACG | | GA | GTAAGCAGGG | GGCACAGGAC | TCAGGGGCGA | CCCGTGCGGG | | | 8561 |
| Lys | Val | Thr | | Glu | | | | | | | |
| | | 340 | | | | | | | | | |

AGGGCCGCCG GGAAAGCACT GGCGAGGGGG CCAGCCTGGA GGAGGAAGGC ATTGAGTGGA 8621
GGACTGGGAG TGAGGAAGTT AGCACCGGTC GGGGTGAGTA TGCACACACC TTCCTGTTGG 8681

```
CACAGGCTGA GTGTCAGTGC CTACTTGATT CCCCCAG G GAG GAC TTC TAC AAG         8734
                                           Glu Asp Phe Tyr Lys
                                                        345

CTG GTC AGT GAG TTC ACA ATC ACC AAG GGG CTC AGA GGC GCC AAG ACG        8782
Leu Val Ser Glu Phe Thr Ile Thr Lys Gly Leu Arg Gly Ala Lys Thr
            350                 355                 360

ACC TTT GAT GTC TAC ACC GAG TCC TGG GCC CAG GAC CCA TCC CAG GAG        8830
Thr Phe Asp Val Tyr Thr Glu Ser Trp Ala Gln Asp Pro Ser Gln Glu
            365                 370                 375

AAT AAG AAG AAG ACT GTG GTG GAC TTT GAG ACC GAT GTC CTC TTC CTG        8878
Asn Lys Lys Lys Thr Val Val Asp Phe Glu Thr Asp Val Leu Phe Leu
            380                 385                 390

GTG CCC ACC GAG ATT GCC CTA GCC CAG CAC AGA GCC AAT GCC      AA        8922
Val Pro Thr Glu Ile Ala Leu Ala Gln His Arg Ala Asn Ala      Lys
395                 400                 405

GTGAGGATCT GGGCAGCGGG TGGCTCCTGG GGGCCTTCCT GGGGTGCTGC ACCTTCCAGC      8982
CGAGGCCTCG CTGTGGGTGG CTCTCAGGTG TCTGGGTTGT CTGGGAAAGT GGTGCTTGAG      9042
TCCCCACCTG TGCCTGCCTG ATCCACTTTG CTGAGGCCTG GCAAGACTTG AGGGCCTCTT      9102
TTTACCTCCC AGCCTACAGG GCTTACAAA  CCCTATGATC CTCTGCCCTG CTCAGCCCTG      9162
CACCCCATGG TCCTTCCCAC TGGAGAGTTC TTGAGCTACC TTCCATCCCC CATGCTGTGT      9222
GCACTGAGAG AACACTGGAC AATAGTTTCT ATCCACTGAC TCTTATGGGC CTCAACTTTG      9282
CCCATAATTT CAGCCCACCA CCACATTAAA AATCTTCATG TAATAATAGC CAATTATAAT      9342
AAAAAATAAG GCCAGACACA GTAGCTCATG CCTGTAATCC AGCACATTG  GGAGGTCAAG      9402
GTGGGAGGAT CACTTGAGGT CAGGAGTCTG AGACTAGTCT GGCCAACATG GCAAAACCCC      9462
ATCTCTACTA AAAATACAAA AATTATCCAG GCATGGTGGT GCATGCCTAT AATCCAGCT       9522
ACTCAGGAGG CTGAGGTAGC AGAATTGATT GACCCAGGGA GGTGGAGGTT GCAGTGAGCC      9582
GAGATTACGC CACTGCACTC CAGCAGGGGC AACAGAGTGA GACTGTGTCT CGAATAAATA      9642
AGTAAATAAA TAATAAAAAT AAAAAATAAG TTAGGAATAC GAAAAAGATA GGAAGATAAA      9702
AGTATACCTA GAAGTCTAGG ATGAAAGCTT TGCAGCAACT AAGCAGTACA TTTAGCTGTG      9762
AGCCTCCTTT CAGTCAAGGC AAAAAGGGAA ACAGTTGAGG GCCTATACCT TGTCCAATCT      9822
AATTGAAGAA TGCACATTCA CTTGGAGAGC AAAATATTTC TTGATACTGA ATTCTAGAAG      9882
GAAGGTGCCT CACAATGTTT TGTGGAGGTG AAGTATAAAT TCAGCTGAAA TTGTGGAACC      9942
CATGAATCCA TGAATTTGGT TCTCAGCTTT CCCTTCCCTG GGTGTAAGAA GCCCCATCTC      10002
TTCATGTGAA TTCCCCAGAC ACTTCCCTGC CCACTGCCCG GGACCTCCCT CCAAGTCCGG      10062
TCTCTGGGCT GATCGGTCCC CAGTGAGCAC CCTGCCTACT TGGGTGGTCT CTCCCCTCCA      10122

G G AGT GCC AAG ACC TAC GCC TAC CTG TTT TCC CAT CCC TCT CGG ATG        10169
  Ser Ala Lys Thr Tyr Ala Tyr Leu Phe Ser His Pro Ser Arg Met
  410                 415                 420

CCC GTC TAC CCC AAA TGG GTG GGG GCC GAC CAT GCA GAT GAC ATT CAG        10217
Pro Val Tyr Pro Lys Trp Val Gly Ala Asp His Ala Asp Asp Ile Gln
425                 430                 435                 440

TAC GTT TTC GGG AAG CCC TTC GCC ACC CCC ACG GGC TAC CGG CCC CAA        10265
Tyr Val Phe Gly Lys Pro Phe Ala Thr Pro Thr Gly Tyr Arg Pro Gln
            445                 450                 455

GAC AGG ACA GTC TCT AAG GCC ATG ATC GCC TAC TGG ACC AAC TTT GCC        10313
Asp Arg Thr Val Ser Lys Ala Met Ile Ala Tyr Trp Thr Asn Phe Ala
            460                 465                 470

AAA ACA    GG GTAAGACGTG GGTTGAGTGC AGGGCGGAGG GCCACAGCCG              10361
Lys Thr    Gly
           475
```

```
AGAAGGGCCT CCCACCACGA GGCCTTGTTC CCTCATTTGC CAGTGGAGGG ACTTTGGGCA    10421

AGTCACTTAA CCTCCCCCTG CATCGGAATC CATGTGTGTT TGAGGATGAG AGTTACTGGC    10481

AGAGCCCCAA GCCCATGCAC GTGCACAGCC AGTGCCCAGT ATGCAGTGAG GGGCATGGTG    10541

CCCAGGGCCA GCTCAGAGGG CGGGGATGGC TCAGGCGTGC AGGTGGAGAG CAGGGCTTCA    10601

GCCCCCTGGG AGTCCCCAGC CCCTGCACAG CCTCTTCTCA CTCTGCAG G GAC CCC       10656
                                                     Asp Pro

AAC ATG GGC GAC TCG GCT GTG CCC ACA CAC TGG GAA CCC TAC ACT ACG    10704
Asn Met Gly Asp Ser Ala Val Pro Thr His Trp Glu Pro Tyr Thr Thr
        480             485             490

GAA AAC AGC GGC TAC CTG GAG ATC ACC AAG AAG ATG GGC AGC AGC TCC    10752
Glu Asn Ser Gly Tyr Leu Glu Ile Thr Lys Lys Met Gly Ser Ser Ser
    495             500             505

ATG AAG CGG AGC CTG AGA ACC AAC TTC CTG CGC TAC TGG ACC CTC ACC    10800
Met Lys Arg Ser Leu Arg Thr Asn Phe Leu Arg Tyr Trp Thr Leu Thr
510             515             520             525

TAT CTG GCG CTG CCC ACA GTG ACC GAC CAG GAG GCC ACC CCT GTG CCC    10848
Tyr Leu Ala Leu Pro Thr Val Thr Asp Gln Glu Ala Thr Pro Val Pro
                530             535             540

CCC ACA GGG GAC TCC GAG GCC ACT CCC GTG CCC CCC ACG GGT GAC TCC    10896
Pro Thr Gly Asp Ser Glu Ala Thr Pro Val Pro Pro Thr Gly Asp Ser
            545             550             555

GAG ACC GCC CCC GTG CCG CCC ACG GGT GAC TCC GGG GCC CCC CCC GTG    10944
Glu Thr Ala Pro Val Pro Pro Thr Gly Asp Ser Gly Ala Pro Pro Val
        560             565             570

CCG CCC ACG GGT GAC TCC GGG GCC CCC GTG CCG CCC ACG GGT GAC    10992
Pro Pro Thr Gly Asp Ser Gly Ala Pro Pro Val Pro Pro Thr Gly Asp
    575             580             585

TCC GGG GCC CCC CCC GTG CCG CCC ACG GGT GAC TCC GGG GCC CCC CCC    11040
Ser Gly Ala Pro Pro Val Pro Pro Thr Gly Asp Ser Gly Ala Pro Pro
590             595             600             605

GTG CCG CCC ACG GGT GAC TCC GGG GCC CCC GTG CCG CCC ACG GGT    11088
Val Pro Pro Thr Gly Asp Ser Gly Ala Pro Pro Val Pro Pro Thr Gly
                610             615             620

GAC TCC GGG GCC CCC CCC GTG CCG CCC ACG GGT GAC TCC GGC GCC CCC    11136
Asp Ser Gly Ala Pro Pro Val Pro Pro Thr Gly Asp Ser Gly Ala Pro
            625             630             635

CCC GTG CCG CCC ACG GGT GAC GCC GGG CCC CCC CCC GTG CCG CCC ACG    11184
Pro Val Pro Pro Thr Gly Asp Ala Gly Pro Pro Pro Val Pro Pro Thr
        640             645             650

GGT GAC TCC GGC GCC CCC CCC GTG CCG CCC ACG GGT GAC TCC GGG GCC    11232
Gly Asp Ser Gly Ala Pro Pro Val Pro Pro Thr Gly Asp Ser Gly Ala
    655             660             665

CCC CCC GTG ACC CCC ACG GGT GAC TCC GAG ACC GCC CCC GTG CCG CCC    11280
Pro Pro Val Thr Pro Thr Gly Asp Ser Glu Thr Ala Pro Val Pro Pro
670             675             680             685

ACG GGT GAC TCC GGG GCC CCC CCT GTG CCC CCC ACG GGT GAC TCT GAG    11328
Thr Gly Asp Ser Gly Ala Pro Pro Val Pro Pro Thr Gly Asp Ser Glu
                690             695             700

GCT GCC CCT GTG CCC CCC ACA GAT GAC TCC AAG GAA GCT CAG ATG CCT    11376
Ala Ala Pro Val Pro Pro Thr Asp Asp Ser Lys Glu Ala Gln Met Pro
            705             710             715

GCA GTC ATT AGG TTT TAGCGTCCCA TGAGCCTTGG TATCAAGAGG CCACAAGAGT    11431
Ala Val Ile Arg Phe
        720

GGGACCCCAG GGGCTCCCCT CCCATCTTGA GCTCTTCCTG AATAAAGCCT CATACCCCTG    11491

TCGGTGTCTT TCTTTGCTCC CAAGGCTAAG CTGCAGGATC                         11531
```

( 2 ) INFORMATION FOR SEQ ID NO:2:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( i v ) ANTI-SENSE: YES ( x i ) SEQUENCE DESCRIPTION: SEQ ID NO:2:

AGGTGAGGCC CAACACAACC AGTTGC      26

( 2 ) INFORMATION FOR SEQ ID NO:3:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

GATCGTCGAC      10

( 2 ) INFORMATION FOR SEQ ID NO:4:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

CGTCGACGTA C      11

( 2 ) INFORMATION FOR SEQ ID NO:5:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

GTCGACGGTA C      11

( 2 ) INFORMATION FOR SEQ ID NO:6:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

AGACCTACGC CTACCTG      17

( 2 ) INFORMATION FOR SEQ ID NO:7:

(i) SEQUENCE CHARACTERISTICS:
　　　　(A) LENGTH: 17 base pairs
　　　　(B) TYPE: nucleic acid
　　　　(C) STRANDEDNESS: single
　　　　(D) TOPOLOGY: linear (ii) MOLECULE TYPE: DNA (genomic)

(xi) SEQUENCE DESCRIPTION: SEQ ID NO:7:

TCCAGTAGGC GATCATG　　　　　　　　　　　　　　　　　　　　　　　　　17

(2) INFORMATION FOR SEQ ID NO:8:

(i) SEQUENCE CHARACTERISTICS:
　　　　(A) LENGTH: 20 base pairs
　　　　(B) TYPE: nucleic acid
　　　　(C) STRANDEDNESS: single
　　　　(D) TOPOLOGY: linear (ii) MOLECULE TYPE: DNA (genomic)

(xi) SEQUENCE DESCRIPTION: SEQ ID NO:8:

GACCGATGTC CTCTTCCTGG　　　　　　　　　　　　　　　　　　　　　　　20

(2) INFORMATION FOR SEQ ID NO:9:

(i) SEQUENCE CHARACTERISTICS:
　　　　(A) LENGTH: 20 base pairs
　　　　(B) TYPE: nucleic acid
　　　　(C) STRANDEDNESS: single
　　　　(D) TOPOLOGY: linear (ii) MOLECULE TYPE: DNA (genomic)

(xi) SEQUENCE DESCRIPTION: SEQ ID NO:9:

CAGCCGAGTC GCCCATGTTG　　　　　　　　　　　　　　　　　　　　　　　20

(2) INFORMATION FOR SEQ ID NO:10:

(i) SEQUENCE CHARACTERISTICS:
　　　　(A) LENGTH: 21 base pairs
　　　　(B) TYPE: nucleic acid
　　　　(C) STRANDEDNESS: single
　　　　(D) TOPOLOGY: linear (ii) MOLECULE TYPE: DNA (genomic)

(xi) SEQUENCE DESCRIPTION: SEQ ID NO:10:

ACCAAGAAGA TGGGCAGCAG C　　　　　　　　　　　　　　　　　　　　　21

(2) INFORMATION FOR SEQ ID NO:11:

(i) SEQUENCE CHARACTERISTICS:
　　　　(A) LENGTH: 21 base pairs
　　　　(B) TYPE: nucleic acid
　　　　(C) STRANDEDNESS: single
　　　　(D) TOPOLOGY: linear (ii) MOLECULE TYPE: DNA (genomic)

(xi) SEQUENCE DESCRIPTION: SEQ ID NO:11:

GACTGCAGGC ATCTGAGCTT C　　　　　　　　　　　　　　　　　　　　　21

(2) INFORMATION FOR SEQ ID NO:12:

(i) SEQUENCE CHARACTERISTICS:
　　　　(A) LENGTH: 15 base pairs
　　　　(B) TYPE: nucleic acid
　　　　(C) STRANDEDNESS: single
　　　　(D) TOPOLOGY: linear (i i) MOLECULE TYPE: DNA (genomic)

(x i) SEQUENCE DESCRIPTION: SEQ ID NO:12:

GCCGCGAAGG TAAGA  15

(2) INFORMATION FOR SEQ ID NO:13:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:13:

GTGTCTCCCT CGCAGCTGGG CGCC  24

(2) INFORMATION FOR SEQ ID NO:14:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:14:

TGGCAAGGTG GGA  13

(2) INFORMATION FOR SEQ ID NO:15:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:15:

TCCTGCCACC TGCAGGGACC CTG  23

(2) INFORMATION FOR SEQ ID NO:16:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:16:

AAGCAAGGTC TGC  13

(2) INFORMATION FOR SEQ ID NO:17:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:17:

GCTCCCCCAT CTCAGTCTCC CGG 23

( 2 ) INFORMATION FOR SEQ ID NO:18:

( i ) SEQUENCE CHARACTERISTICS:
  ( A ) LENGTH: 13 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:18:

CTGCCAGGTG CGT 13

( 2 ) INFORMATION FOR SEQ ID NO:19:

( i ) SEQUENCE CHARACTERISTICS:
  ( A ) LENGTH: 23 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:19:

CTGCCCTGCC CCAGGTAAC TAT 23

( 2 ) INFORMATION FOR SEQ ID NO:20:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:20:

TCTCTGCAGG TCTCG 15

( 2 ) INFORMATION FOR SEQ ID NO:21:

( i ) SEQUENCE CHARACTERISTICS:
  ( A ) LENGTH: 24 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:21:

TTCTGGGTCC CGTAGACCCT CTCC 24

( 2 ) INFORMATION FOR SEQ ID NO:22:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:22:

GCCAAAAAGG TAAAC 15

( 2 ) INFORMATION FOR SEQ ID NO:23:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:23:

TGGTTCTGCC CCCAGGTGGC TGAG                                            24

( 2 ) INFORMATION FOR SEQ ID NO:24:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:24:

CTGGAGTGTG AGT                                                        13

( 2 ) INFORMATION FOR SEQ ID NO:25:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:25:

GGCTCTCCCA CCCAGACCCC ATG                                             23

( 2 ) INFORMATION FOR SEQ ID NO:26:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:26:

GTCACGGAGT AAGC                                                       14

( 2 ) INFORMATION FOR SEQ ID NO:27:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:27:

ACTTGATTCC CCCAGGGAGG AC                                              22

( 2 ) INFORMATION FOR SEQ ID NO:28:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:28:

AATGCCAAGT GAGG    14

( 2 ) INFORMATION FOR SEQ ID NO:29:

( i ) SEQUENCE CHARACTERISTICS:
      ( A ) LENGTH: 22 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:29:

GTCTCTCCCC TCCAGGAGTG CC    22

( 2 ) INFORMATION FOR SEQ ID NO:30:

( i ) SEQUENCE CHARACTERISTICS:
      ( A ) LENGTH: 14 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:30:

AAAACAGGGT AAGA    14

( 2 ) INFORMATION FOR SEQ ID NO:31:

( i ) SEQUENCE CHARACTERISTICS:
      ( A ) LENGTH: 22 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:31:

CTTCTCACTC TGCAGGGACC CC    22

( 2 ) INFORMATION FOR SEQ ID NO:32:

( i ) SEQUENCE CHARACTERISTICS:
      ( A ) LENGTH: 1640 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:32:

```
GGATCCCTCG AACCCAGGAG TTCAAGACTG CAGTGAGCTA TGATTGTGCC ACTGCACTCT      60
AGCCTGGGTG ACAGAGACCC TGTCTCAAAA AAACAAACAA ACAAAAAACC TCTGTGGACT     120
CCGGGTGATA ATGACATGTC AATGTGGATT CATCAGGTGT TAACAGCTGT ACCCCCTGGT     180
GGGGATGTT GATAACGGGG GAGACTGGAG TGGGCGAGG ACATACGGGA AATCTCTGTA       240
ATCTTCCTCT AATTTTGCTG TGAACCTAAA GCTGCTCTAA AAATGTACAT AGATATAAAC     300
TGGGCCTTC CTTTCCCTCT GCCCTGCCCC AGCCCTCCCC CACCTCCTTC CTCTCCCTGC      360
TGCCTCCCCT CTGCCCTCCC CTTTCCTCCT TAGCCACTGT AAATGACACT GCAGCAAAGG     420
TCTGAGGCAA ATGCCTTTGC CCTGGGGCGC CCCAGCCACC TGCAGGCCCC TTATTTCCTG     480
```

```
TGGCCGAGCT CCTCCTCCCA CCCTCCAGTC CTTTCCCCAG CCTCCCTCGC CCACTAGGCC      540

TCCTGAATTG CTGGCACCGG CTGTGGTCGA CAGACAGAGG GACAGACGTG GCTCTGCAGG      600

TCCACTCGGT CCCTGGCACC GGCCGCAGGG GTGGCAGAAC GGGAGTGTGG TTGGTGTGGG      660

AAGCACAGGC CCCAGTGTCT CCTGGGGGAC TGTTGGGTGG GAAGGCTCTG GCTGCCCTCA      720

CCCTGTTCCC ATCACTGCAG AGGGCTGTGC GGTGGCTGGA GCTGCCACTG AGTGTCTCGG      780

TGAGGGTGAC CTCACACTGG CTGAGCTTAA AGGCCCCATC TGAAGACTTT GTTCGTGGTG      840

TTCTTTCACT TCTCAGAGCC TTTCCTGGCT CCAGGATTAA TACCTGTTCA CAGAAAATAC      900

GAGTCGCCTC CTCCTCCACA ACCTCACACG ACCTTCTCCC TTCCCTCCCG CTGGCCTCTT      960

TCCCTCCCCT TCTGTCACTC TGCCTGGGCA TGCCCCAGGG CCTCGGCTGG GCCCTTTGTT     1020

TCCACAGGGA AACCTACATG GTTGGGCTAG ATGCCTCCGC ACCCCCCAC CCACACCCCC     1080

TGAGCCTCTA GTCCTCCCTC CCAGGACACA TCAGGCTGGA TGGTGACACT TCCACACCCT     1140

TGAGTGGGAC TGCCTTGTGC TGCTCTGGGA TTCGCACCCA GCTTGGACTA CCCGCTCCAC     1200

GGGCCCCAGG AAAAGCTCGT ACAGATAAGG TCAGCCACAT GAGTGGAGGG CCTGCAGCAT     1260

GCTGCCCTTT CTGTCCAGA AGTCACGTGC TCGGTCCCCT CTGAAGCCCC TTTGGGGACC     1320

TAGGGACAA GCAGGGCATG GAGACATGGA GACAAAGTAT GCCCTTTTCT CTGACAGTGA     1380

CACCAAGCCC TGTGAACAAA CCAGAAGGCA GGGCACTGTG CACCCTGCCC GGCCCCACCA     1440

TCCCCCTTAC CACCCGCCAC CTTGCCACCT GCCTCTGCTC CCAGGTAAGT GGTAACCTGC     1500

ACAGGTGCAC TGTGGGTTTG GGGAAAACTG GATCTCCCTG CACCTGAGGG GGTAGAGGGG     1560

AGGGAGTGCC TGAGAGCTCA TGAACAAGCA TGTGACCTTG GATCCAGCTC CATAAATACC     1620

CGAGGCCCAG GGGGAGGGCC                                                 1640
```

( 2 ) INFORMATION FOR SEQ ID NO:33:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:33:

```
GGTACATGTT CT                                                           12
```

( 2 ) INFORMATION FOR SEQ ID NO:34:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:34:

```
AGGTCATGAC CT                                                           12
```

( 2 ) INFORMATION FOR SEQ ID NO:35:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear (i i) MOLECULE TYPE: DNA (genomic)

(x i) SEQUENCE DESCRIPTION: SEQ ID NO:35:

AAGAAGGAAG T    11

(2) INFORMATION FOR SEQ ID NO:36:

(i) SEQUENCE CHARACTERISTICS:
        (A) LENGTH: 9 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:36:

ATTCTTGGA    9

(2) INFORMATION FOR SEQ ID NO:37:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:37:

AGTTCTTGGC A    11

(2) INFORMATION FOR SEQ ID NO:38:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:38:

GTCACCTGTG CTTTTCCCTG    20

(2) INFORMATION FOR SEQ ID NO:39:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:39:

TGACCTTGGA TCCAGCTCCA TAAATACCCG AG    32

(2) INFORMATION FOR SEQ ID NO:40:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:40:

TGACCTTGGT TCCAGCTCCA TAAATACTGG AG    32

( 2 ) INFORMATION FOR SEQ ID NO:41:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:41:

CACAGGTGCA CTGTGGGTT                                                               19

( 2 ) INFORMATION FOR SEQ ID NO:42:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:42:

CACAGGTGCA CTCCGGGTT                                                               19

( 2 ) INFORMATION FOR SEQ ID NO:43:

( i ) SEQUENCE CHARACTERISTICS:
        ( A ) LENGTH: 7 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:43:

CCTTGCC                                                                                   7

( 2 ) INFORMATION FOR SEQ ID NO:44:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:44:

ACCTGCCTCT GCTCCCAGGT                                                             20

( 2 ) INFORMATION FOR SEQ ID NO:45:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:45:

CCATGCCGAC CGGCCTCTGC TCCCAGGT                                      28

( 2 ) INFORMATION FOR SEQ ID NO:46:

( i ) SEQUENCE CHARACTERISTICS:

(A) LENGTH: 33 base pairs
                (B) TYPE: nucleic acid
                (C) STRANDEDNESS: single
                (D) TOPOLOGY: linear (ii) MOLECULE TYPE: DNA (genomic)

(xi) SEQUENCE DESCRIPTION: SEQ ID NO:46:

GCACTGTGCA CCCTGCCCGG CCCCACCATC CCC    33

(2) INFORMATION FOR SEQ ID NO:47:

(i) SEQUENCE CHARACTERISTICS:
                (A) LENGTH: 5 base pairs
                (B) TYPE: nucleic acid
                (C) STRANDEDNESS: single
                (D) TOPOLOGY: linear (ii) MOLECULE TYPE: DNA (genomic)

(xi) SEQUENCE DESCRIPTION: SEQ ID NO:47:

GCACT    5

(2) INFORMATION FOR SEQ ID NO:48:

(i) SEQUENCE CHARACTERISTICS:
                (A) LENGTH: 25 base pairs
                (B) TYPE: nucleic acid
                (C) STRANDEDNESS: single
                (D) TOPOLOGY: linear (ii) MOLECULE TYPE: DNA (genomic)

(xi) SEQUENCE DESCRIPTION: SEQ ID NO:48:

CAGCCAGCCC TCCCCCACCC TTCCC    25

(2) INFORMATION FOR SEQ ID NO:49:

(i) SEQUENCE CHARACTERISTICS:
                (A) LENGTH: 10 base pairs
                (B) TYPE: nucleic acid
                (C) STRANDEDNESS: single
                (D) TOPOLOGY: linear (ii) MOLECULE TYPE: DNA (genomic)

(xi) SEQUENCE DESCRIPTION: SEQ ID NO:49:

TGACAGTGAC    10

(2) INFORMATION FOR SEQ ID NO:50:

(i) SEQUENCE CHARACTERISTICS:
                (A) LENGTH: 10 base pairs
                (B) TYPE: nucleic acid
                (C) STRANDEDNESS: single
                (D) TOPOLOGY: linear (ii) MOLECULE TYPE: DNA (genomic)

(xi) SEQUENCE DESCRIPTION: SEQ ID NO:50:

TGACACTAAC    10

(2) INFORMATION FOR SEQ ID NO:51:

(i) SEQUENCE CHARACTERISTICS:
                (A) LENGTH: 15 base pairs
                (B) TYPE: nucleic acid
                (C) STRANDEDNESS: single
                (D) TOPOLOGY: linear ( i i ) MOLECULE TYPE: DNA (genomic)

( x i ) SEQUENCE DESCRIPTION: SEQ ID NO:51:

TCTGTCCCAG AAGTC        15

( 2 ) INFORMATION FOR SEQ ID NO:52:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:52:

TCTGGCTCAG GAGTC        15

( 2 ) INFORMATION FOR SEQ ID NO:53:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:53:

TCAGCCACAT GAGTG        15

( 2 ) INFORMATION FOR SEQ ID NO:54:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:54:

TCAGCCACAC CAGTG        15

( 2 ) INFORMATION FOR SEQ ID NO:55:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:55:

CTGCCTTGTG C        11

( 2 ) INFORMATION FOR SEQ ID NO:56:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:56:

CTGCCTCCTG C        11

( 2 ) INFORMATION FOR SEQ ID NO:57:

( i ) SEQUENCE CHARACTERISTICS:
       ( A ) LENGTH: 25 base pairs
       ( B ) TYPE: nucleic acid
       ( C ) STRANDEDNESS: single
       ( D ) TOPOLOGY: linear ( i i ) MOLECULE TYPE: DNA (genomic)

( x i ) SEQUENCE DESCRIPTION: SEQ ID NO:57:

CTGTGTGGCA AGAAGGAAGT GTTGT                                    2 5

( 2 ) INFORMATION FOR SEQ ID NO:58:

( i ) SEQUENCE CHARACTERISTICS:
       ( A ) LENGTH: 22 base pairs
       ( B ) TYPE: nucleic acid
       ( C ) STRANDEDNESS: single
       ( D ) TOPOLOGY: linear ( i i ) MOLECULE TYPE: DNA (genomic)

( x i ) SEQUENCE DESCRIPTION: SEQ ID NO:58:

CAACTCCTGA CCTCAAGTGA TC                                       2 2

TRANSGENIC NON-HUMAN MAMMALS THAT EXPRESS HUMAN BSSL/CEL

This application is a divisional of application Ser. No. 08/068,945, filed on May 27, 1993, now U.S. Pat. No. 5,616,483.

TECHNICAL FIELD

The present invention relates to a DNA molecule containing intron sequences and encoding a human protein which is, depending on the site of action, called Bile Salt-Stimulated Lipase (BSSL) or Carboxyl Ester Lipase (CEL). The DNA molecule is advantageously used in the production of recombinant human BSSL/CEL, preferably by means of production in transgenic non-human mammals. The recombinant human BSSL/CEL can be used as a constituent of infant formulas used for feeding infants as a substitute for human milk, or in the manufacture of medicaments against e.g. fat malabsorption, cystic fibrosis and chronic pancreatitis.

BACKGROUND OF THE INVENTION

Hydrolysis of dietary lipids

Dietary lipids are an important source of energy. The energy-rich triacylglycerols constitute more than 95% of these lipids. Some of the lipids, e.g. certain fatty acids and the fat-soluble vitamins, are essential dietary constituents. Before gastro-intestinal absorption the triacylglycerols as well as the minor components, i.e. esterified fat-soluble vitamins and cholesterol, and diacylphosphatidylglycerols, require hydrolysis of the ester bonds to give rise to less hydrophobic, absorbable products. These reactions are catalyzed by a specific group of enzymes called lipases.

In the human adult the essential lipases involved are considered to be Gastric Lipase, Pancreatic Colipase-Dependent Lipase (hydrolysis of tri- and diacylglycerols), Pancreatic Phospholipase A2 (hydrolysis of diacylphosphatidylglycerols) and Carboxylic Ester Lipase (CEL) (hydrolysis of cholesteryl- and fat soluble vitamin esters). In the breast-fed newborn, Bile Salt-Stimulated Lipase (BSSL) plays an essential part in the hydrolysis of several of the above mentioned lipids. Together with bile salts the products of lipid digestion form mixed micelles from which absorption occurs.

Bile Salt-Stimulated Lipase

The human lactating mammary gland synthesizes and secretes with the milk a Bile Salt-Stimulated Lipase (BSSL) (Blackberg et al., 1987) that, after specific activation by primary bile salts, contributes to the breast-fed infant's endogenous capacity of intestinal fat digestion. This enzyme, which accounts for approximately 1% of total milk protein (Blackberg & Hernell, 1981), is not degraded during passage with the milk through the stomach, and in duodenal contents it is protected by bile salts from inactivation by pancreatic proteases such as trypsin and chymotrypsin. It is, however, inactivated when the milk is pasteurized, e.g. heated to 62.5° C., 30 min (Björksten et al., 1980).

Model experiments in vitro suggest that the end products of triacylglycerol digestion are different in the presence of BSSL (Bernbäck et al., 1990; Hernell & Blackberg, 1982). Due to lower intraluminal bile salt concentrations during the neonatal period this may be beneficial to product absorption.

Carboxylic Ester Lipase

The Carboxylic Ester Lipase (CEL) of human pancreatic juice (Lombardo et al., 1978) seems functionally to be identical, or at least very similar, to BSSL (Blackberg et al., 1981). They also share common epitopes, have identical N-terminal amino acid sequences (Abouakil et al., 1988) and are inhibited by inhibitors of serine esterases, e.g. eserine and diisopropylfluorophopsphate. In recent studies from several laboratories the cDNA structures from both the milk lipase and the pancreas lipase have been characterized (Baba et al., 1991; Hui et al., 1990; Nilsson et al., 1990; Reue et al., 1991) and the conclusion is that the milk enzyme and the pancreas enzyme are products of the same gene (in this application referred to as the CEL gene, EC 3.1.1.1). The cDNA sequence and deduced amino acid sequence of the CEL gene are described in WO 91/15234 (Oklahoma Medical Research Foundation) and in WO 91/18923 (Aktiebolaget Astra).

CEL is thus assumed to be identical to BSSL, and the polypeptide encoded by the CEL gene is in the present context called BSSL/CEL.

Lipid malabsorption

Common causes of lipid malabsorption, and hence malnutrition, are reduced intraluminal levels of Pancreatic Colipase-Dependent Lipase and/or bile salts. Typical examples of such lipase deficiency are patients suffering from cystic fibrosis, a common genetic disorder resulting in a life-long deficiency in 80% of the patients, and chronic pancreatitis, often due to chronic alcoholism.

The present treatment of patients suffering from a deficiency of pancreatic lipase is the oral administration of very large doses of a crude preparation of porcine pancreatic enzymes. However, Colipase-Dependent Pancreatic Lipase is inactivated by the low pH prevalent in the stomach. This effect cannot be completely overcome by the use of large doses of enzyme. Thus the large doses administered are inadequate for most patients, and moreover the preparations are impure and unpalatable.

Certain tablets have been formulated which pass through the acid regions of the stomach and discharge the enzyme only in the relatively alkaline environment of the jejunum. However, many patients suffering from pancreatic disorders have an abnormally acid jejunum and in those cases the tablets may fail to discharge the enzyme.

Moreover, since the preparations presently on the market are of a non-human source there is a risk of immunoreactions that may cause harmful effects to the patients or result in reduced therapy efficiency. A further drawback with the present preparations is that their content of other lipolytic activities than Colipase-Dependent Lipase are not stated. In fact, most of them contain very low levels of BSSL/CEL-activity. This may be one reason why many patients, suffering from cystic fibrosis in spite of supplementation therapy, suffer from deficiencies of fat soluble vitamins and essential fatty acids.

Thus, there is a great need for products with properties and structure derived from human lipases and with a broad substrate specificity, which products may be orally administered to patients suffering from deficiency of one or several of the pancreatic lipolytic enzymes. Products that can be derived from the use of the present invention fulfil this need by themselves, or in combination with preparations containing other lipases.

Infant formulas

It is well known that human milk-feeding is considered superior to formula-feeding for infants. Not only does human milk provide a well-balanced supply of nutrients, but it is also easily digested by the infant. Thus, several biologically active components which are known to have physiological functions in the infant are either a constituent of human milk or produced during the digestion thereof, including components involved in the defense against infection and components facilitating the uptake of nutrients from human milk.

In spite of the great efforts which have been invested in preparing infant formulas, it has not been possible to produce a formula which to any substantial extent has the advantageous properties of human milk. Thus, infant formulas, often prepared on the basis of cow milk, is generally incompletely digested by the infant and is lacking substances known to have effect on the physiological functions of the infant. In order to obtain an infant formula with a nutritional value similar to human milk, a number of additives including protein fragments, vitamins, minerals etc., which are normally formed or taken up during the infant's digestion of human milk, are included in the formula with the consequent risk of posing an increased strain on and possible long-term damage of important organs such as liver and kidney. Another disadvantage associated with the use of cow milk-based formulas is the increased risk for inducing allergy in the infant against bovine proteins.

As an alternative to cow milk-based infant formulas, human milk obtainable from so-called milk banks has been used. However, feeding newborn infants with human milk from milk banks has in the recent years to an increasing extent been avoided, because of the fear for the presence of infective agents such as HIV and CMV in human milk. In order to destroy the infective agents in human milk it has become necessary to pasteurize the milk before use. However, by pasteurization the nutritional value and the biological effects of the milk components are decreased, for example is BSSL inactivated, as mentioned above.

Addition of lipases to infant formulas

The pancreatic and liver functions are not fully developed at birth, most notably in infants born before term. Fat malabsorption, for physiological reasons, is a common finding and thought to result from low intraluminal Pancreatic Colipase-Dependent Lipase and bile salt concentrations. However, because of BSSL, such malabsorption is much less frequent in breast-fed infants than in infants fed pasteurized human milk or infant formulas (Bernbäck et al., 1990).

To avoid the above disadvantages associated with pasteurized milk and bovine milk-based infant formulas, it would thus be desirable to prepare an infant formula with a composition closer to that of human milk, i.e. a formula comprising human milk proteins.

BSSL/CEL has several unique properties that makes it ideally suited for supplementation Of infant formulas:

It has been designed by nature for oral administration. Thus, it resists passage through the stomach and is activated in contents of the small intestine.

Its specific activation mechanism should prevent hazardous lipolysis of food or tissue lipids during storage and passage to its site of action.

Due to its broad substrate specificity it has the potential to, on its own, mediate complete digestion of most dietary lipids, including the fat soluble vitamin esters.

BSSL/CEL may be superior to Pancreatic Colipase-Dependent Lipase to hydrolyze ester bonds containing long-chain polyunsaturated fatty acids.

In the presence of Gastric Lipase and in the absence of, or at low levels of Colipase-Dependent Lipase, BSSL/CEL can ascertain a complete triacylglycerol digestion in vitro even if the bile salt levels are low such as in newborn infants. In the presence of BSSL/CEL the end products of triacylglycerol digestion become free fatty acids and free glycerol rather than free fatty acids and monoacylglycerol generated by the other two lipases (Bernbäck et al., 1990). This may favour product absorption particularly when the intraluminal bile salt levels are low.

The utilization of BSSL/CEL for supplementation of infant formulas requires however access to large quantities of the product. Although human milk proteins may be purified directly from human milk, this is not a realistic and sufficiently economical way to obtain the large quantities needed for large scale formula production, and other methods must consequently be developed before an infant formula comprising human milk proteins may be prepared. The present invention provides such methods for preparation of BSSL/CEL in large quantities.

Production of proteins in milk of transgenic animals

The isolation of genes encoding pharmacologically active proteins has permitted cheaper production of such proteins in heterologous systems. An appealing expression system for milk proteins is the transgenic animal (For a review see Hennighausen et al., 1990). Dietary compositions comprising bile salt-activated lipase derived from e.g. transgenic animal technology, is described in EP 317,355 (Oklahoma Medical Research Foundation).

In the transgenic animal, the protein coding sequence can be introduced as cDNA or as a genomic sequence. Since introns may be necessary for regulated gene expression in transgenic animals (Brinster et al., 1988; Whitelaw et al., 1991) it is in many cases preferable to use the genomic form rather than the cDNA form of the structural gene. WO 90/05188 (Pharmaceutical Proteins Limited) describes the use in transgenic animals of protein-coding DNA comprising at least one, but not all, of the introns naturally occurring in a gene coding for the protein.

PURPOSE OF THE INVENTION

It is an object of the present invention to provide a means for producing recombinant human BSSL/CEL, in a high yield and at a realistic price, for use in infant formulas in order to avoid the disadvantages with pasteurized milk and formulas based on bovine proteins.

BRIEF DESCRIPTION OF THE INVENTION

The purpose of the invention has been achieved by cloning and sequencing the human CEL gene. In order to improve the yield of BSSL/CEL, the obtained DNA molecule containing intron sequences, instead of the known cDNA sequence, of the human CEL gene has been used for production of human BSSL/CEL in a transgenic non-human mammal.

Accordingly, in one aspect the present invention relates to a DNA molecule shown in the Sequence Listing as SEQ ID NO: 1, or an analogue of the said DNA molecule which hybridizes with the DNA molecule shown in the Sequence Listing as SEQ ID NO: 1, or a specific part thereof, under stringent hybridization conditions.

The procedure used for isolating the human BSSL/CEL DNA molecule is outlined in the Examples below.

The stringent hybridization conditions referred to above are to be understood in their conventional meaning, i.e. that hybridization is carried out according to an ordinary laboratory manual such as Sambrook et al. (1989).

In another aspect the present invention provides a mammalian expression System comprising a DNA sequence encoding human BSSL/CEL inserted into a gene encoding a milk protein of a non-human mammal so as to form a hybrid gene which is expressible in the mammary gland of an adult female of a mammal harbouring said hybrid gene so that human BSSL/CEL is produced when the hybrid gene is expressed.

In yet a further aspect, the present invention relates to a method of producing a transgenic non-human mammal capable of expressing human BSSL/CEL, comprising injecting a mammalian expression system as defined above into a fertilized egg or a cell of an embryo of a mammal so as to incorporate the expression system into the germline of the mammal and developing the resulting injected fertilized egg or embryo into an adult female mammal.

FIGURE LEGENDS

FIG. 1

The CEL gene locus. Localization and restriction enzyme map of the two partly overlapping clones, λBSSL1 and λBSSL5A are shown. The exon-intron organization and used restriction enzyme site are shown below. Exons are represented by boxes numbered 1-11. Asp=Asp700, B=BamHI, E=EcoRI, S=SacI, Sa=SalI, Sp=SphI and X=XbaI. Positions and orientation of Alu repetitive elements are shown by bold arrows. a-h represent different subcloned fragments.

FIGS. 2A-D

Primer extension analysis of RNA from human lactating mammary gland, pancreas and adipose tissue. An end-radiolabeled 26-mer oligonucleotide, which is complementary to nt positions 33 to 58 of the CEL gene, was used to prime reverse transcription of the RNA. Lane A is a molecular size marker (a sequencing ladder), lane B pancreatic RNA, lane C adipose tissue RNA and lane D lactating mammary gland RNA.

FIGS. 3A-H

Dotplot analysis of the human CEL and rat CEL gene. 5'-flanking regions. The homology regions are labeled A-H and the sequences representing these parts are written, upper is human and lower is rat.

FIG. 4

Analysis of 5'-flanking sequence of the human CEL gene. The putative recognition sequences are either highlighted underline or underline representing the complementary strand. Bold letters show the locations of the homologies to the rCEL (regions A-H). The TATA-box is underlined with dots.

There are two sequences that both show a 80% similarity to the consensus sequence of the glucocorticoid receptor binding site, GGTACANNNTGTTCT, (Beato, M., 1989), the first one on the complementary strand at nt position −231 (1A) and the second one at nt position −811 (1B). Moreover, at nt position −861 (2) there is a sequence that shows 87% similarity to the consensus sequence of the estrogen receptor binding site, AGGTCANNNTGACCT, (Beato, M., 1989).

Lubon and Henninghausen (1987) have analyzed the promoter and 5'-flanking sequences of the whey acidic protein (WAP) gene and established the binding sites for nuclear proteins of lactating mammary gland cells. One of them, an 11 bp conserved sequence, AAGAAGGAAGT, is present in a number of milk protein genes studied e.g. the rat α-lactalbumin gene (Qasba et al., 1984) and the rat α-casein gene (Yu-Lee et al., 1986). In the CEL gene's 5'-flanking region, on the complementary strand at nt position −1299 (3) there is a sequence that shows 82% similarity to this conserved sequence.

In a study of the β-casein gene's regulation, a tissue specific mammary gland factor (MGF) was found in nuclear extracts from pregnant or lactating mice and its recognition sequence was identified (ANTTCTTGGNA). In the human CEL gene's 5'-flanking region there are two sequences, one on the complementary strand at nt position −368 (4A) and the other at nt position −1095 (4B), they both show 82% similarity to the consensus sequence of the MGF binding site. Beside these two putative MGF binding sites in the 5'-flanking region there is a sequence on the complementary strand at nt 275 in intron I, AGTTCTTGGCA, which shows 100% identity to the consensus sequence of the MGF binding site.

Furthermore, there are four sequences which all show 65% similarity to the consensus sequence of rat pancreas-specific enhancer element, GTCACCTGTGCTTTTCCCTG, (Boulet et al., 1986), one at nt position −359 (5A), the second at nt position −718 (5B), the third at nt position −1140 (5C) and the last at nt position −1277 (5D).

FIG. 5

Method for production of the plasmid pS452. For further details, see Example 2.

FIG. 6

Schematic structure of the plasmid pS312.

FIG. 7

Schematic structure of the plasmid pS452.

FIG. 8

Physical map representing the physical introduction of human BSSL/CEL genomic structure in the first exon of the WAP gene as described in Example 2.

FIGS. 9A-C

A. Schematic representation of the localization of PCR-primers used for identification of transgenic animals. The 5'-primer is positioned within the WAP sequence starting at the position −148 bp upstream of the fusion bet, ween the WAP and BSSL/CEL. The 3'-primer is localized in the first BSSL/CEL intron ending 398 bp downstream of the fusion point.

B. The sequences of the PCR primers used,

C. Agarose gel showing a typical analysis of the PCR analysis of the potential founder animals. M: molecular weight markers, Lane 1: control PCR-product generated from the plasmid pS452, Lanes 2-13: PCR reactions done with DNA preparations from potential founder animals,

FIG. 10

Immunoblot analysis of milk from a mouse line transgenic for the recombinant murine WAP/human GEL gene of pS4S2. The proteins were separated on SDS-PAGE, transferred to Immobilon membranes (Millipore) and visualized with polyclonal rabbit antibodies generated using highly purified human native GEL, followed by alkaline phosphatase labelled swine anti-rabbit IgG (Dakopatts). Lane 1, Low molecular weight markers, 106, 80, 49.5, 32.5, 27.5, and 18.5 kDa, respectively. Lane 2, High molecular weight markers, 205, 116.5, 80 and 49.5 kDa, respectively. Lane 3, 25 ng purified non-recombinant GEL from human milk. Lane 4, 2 μl milk sample from a GEL transgenic mouse diluted 1:10. Lanes 5 and 6, 2 μl milk samples from two different non-GEL transgenic mice, diluted 1:10, as control samples.

DETAILED DESCRIPTION OF THE INVENTION

Figure 1:
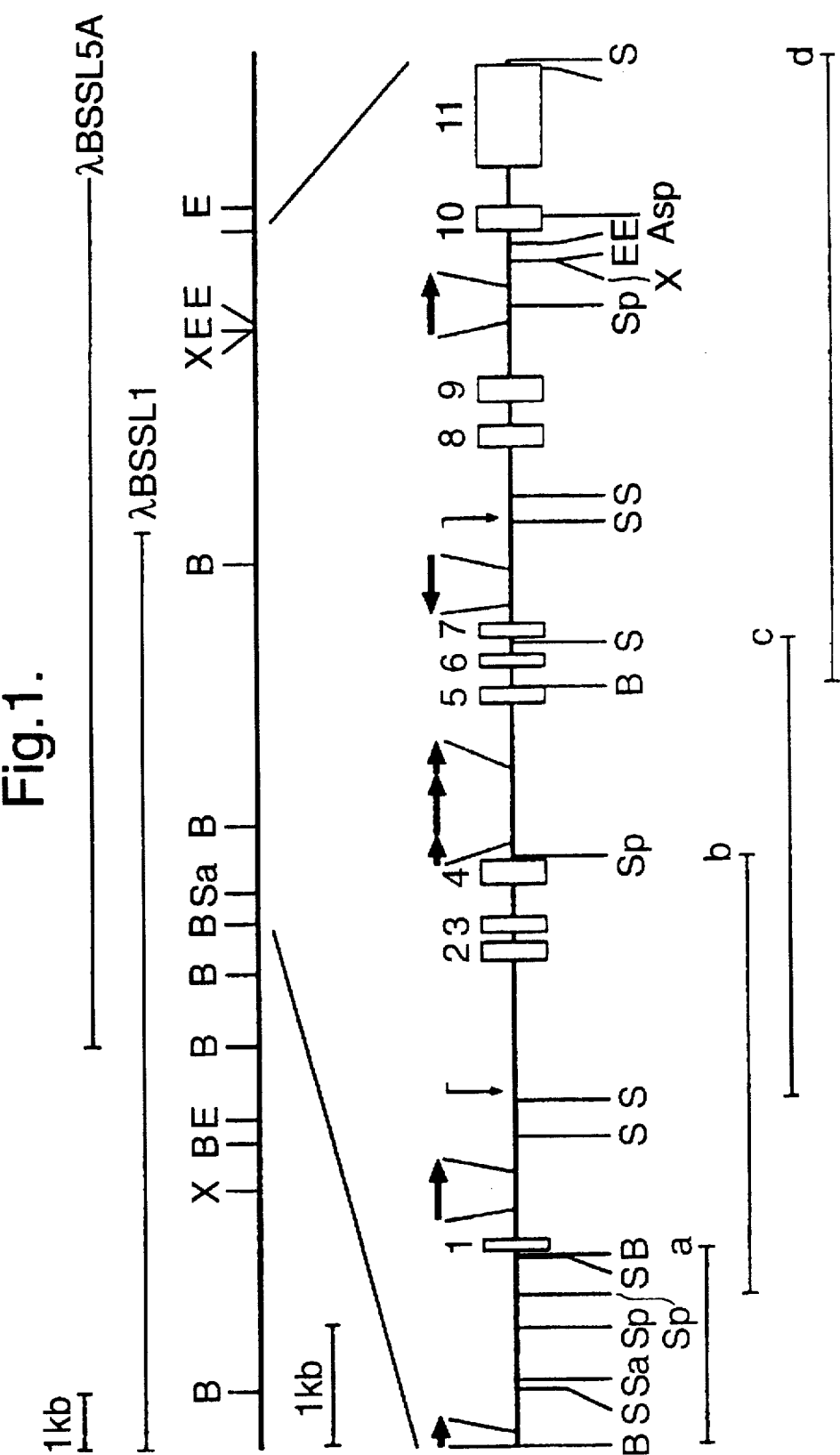

The DNA molecule shown in the Sequence Listing as SEQ ID NO: 1, which has an overall length of 11531 bp, has the following features:

| Feature | from base | to base |
| --- | --- | --- |
| 5'-Flanking region | 1 | 1640 |
| TATA box | 1611 | 1617 |
| Exon 1 | 1641 | 1727 |
| Translation start | 1653 | 1653 |
| Exon 2 | 4071 | 4221 |
| Exon 3 | 4307 | 4429 |
| Exon 4 | 4707 | 4904 |
| Exon 5 | 6193 | 6323 |
| Exon 6 | 6501 | 6608 |
| Exon 7 | 6751 | 6868 |
| Exon 8 | 8335 | 8521 |
| Exon 9 | 8719 | 8922 |
| Exon 10 | 10124 | 10321 |
| Exon 11 | 10650 | 11490 |
| 3'-Flanking region | 11491 | 11531 |

In the present context, the term "gene" is used to indicate a DNA sequence which is involved in producing a polypeptide chain and which includes regions preceding and following the coding region (5'-upstream and 3'-downstream sequences) as well as intervening sequences, the so-called introns, which are placed between individual coding segments (so-called exons) or in the 5'-upstream or 3'-downstream region. The 5'-upstream region comprises a regulatory sequence which controls the expression of the gene, typically a promoter. The 3'-downstream region comprises sequences which are involved in termination of transcription of the gene and optionally sequences responsible for polyadenylation of the transcript and the 3' untranslated region.

The DNA molecules of the invention explained herein may comprise natural as well as synthetic DNA sequences, the natural sequence typically being derived directly from genomic DNA, normally of mammalian origin, e.g. as described below. A synthetic sequence may be prepared by conventional methods for synthetically preparing DNA molecules. The DNA sequence may further be of mixed genomic and synthetic origin.

In a further aspect, the present invention relates to a replicable expression vector which carries and is capable of mediating the expression of a DNA sequence encoding human BSSL/CEL.

In the present context, the term "replicable" means that the vector is able to replicate in a given type of host cell into which it has been introduced. Immediately upstream of the human BSSL/CEL DNA sequence there may be provided a sequence coding for a signal peptide, the presence of which ensures secretion of the human BSSL/CEL expressed by host cells harbouring the vector. The signal sequence may be the one naturally associated with the human BSSL/CEL DNA sequence or of another origin.

The vector may be any vector which may conveniently be subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication; examples of such a vector are a plasmid, phage, cosmid, mini-chromosome or virus. Alternatively, the vector may be one which, when introduced in a host cell, is integrated in the host cell genome and replicated together with the chromosome(s) into which it has been integrated. Examples of suitable vectors are a bacterial expression vector and a yeast expression vector. The vector of the invention may carry any of the DNA molecules of the invention as defined above.

The present invention further relates to a cell harbouring a replicable expression vector as defined above. In principle, this cell may be of any type of cell, i.e. a prokaryotic cell, a unicellular eukaryotic organism or a cell derived from a multicellular organism, e.g. a mammal. The mammalian cells are especially suitable for the purpose and are further discussed below.

In another important aspect, the invention relates to a method of producing recombinant human BSSL/CEL, in which a DNA sequence encoding human BSSL/CEL is inserted in a vector which is able to replicate in a specific host cell, the resulting recombinant vector is introduced into a host cell which is grown in or on an appropriate culture medium under appropriate conditions for expression of human BSSL/CEL and the human BSSL/CEL is recovered.

The medium used to grow the cells may be any conventional medium suitable for the purpose. A suitable vector may be any of the vectors described above, and an appropriate host cell may be any of the cell types listed above. The methods employed to construct the vector and effect introduction thereof into the host cell may be any methods known for such purposes within the field of recombinant DNA. The recombinant human BSSL/CEL expressed by the cells may be secreted, i.e. exported through the cell membrane, dependent on the type of cell and the composition of the vector.

If the human BSSL/CEL is produced intracellularly by the recombinant host, that is, is not secreted by the cell, it may be recovered by standard procedures comprising cell disrupture by mechanical means, e.g. sonication or homogenization, or by enzymatic or chemical means followed by purification.

In order to be secreted, the DNA sequence encoding human BSSL/CEL should be preceded by a sequence coding for a signal peptide, the presence of which ensures secretion of human BSSL/CEL from the cells so that at least a significant proportion of the human BSSL/CEL expressed is secreted into the culture medium and recovered.

The presently preferred method of producing recombinant human BSSL/CEL of the invention is by use of transgenic non-human mammals capable of excreting the human BSSL/CEL into their milk. The use of transgenic non-human mammals has the advantage that large yields of recombinant human BSSL/CEL are obtainable at reasonable costs and, especially when the non-human mammal is a cow, that the recombinant human BSSL/CEL is produced in milk which is the normal constituent of, e.g., infant formulae so that no extensive purification is needed when the recombinant human BSSL/CEL is to be used as a nutrient supplement in milk-based products. Furthermore, production in a higher organism such as a non-human mammal normally leads to the correct processing of the mammalian protein, e.g. with respect to post-translational processing as discussed above and proper folding. Also large quantities of substantially pure human BSSL/CEL may be obtained.

Accordingly, in a further important aspect, the present invention relates to a mammalian expression system comprising a DNA sequence encoding human BSSL/CEL inserted into a gene encoding a milk protein of a non-human mammal so as to form a hybrid gene which is expressible in the mammary gland of an adult female of a mammal harbouring said hybrid gene.

The DNA sequence encoding human BSSL/CEL is preferably a DNA sequence as shown in the Sequence Listing as SEQ ID NO: 1 or a genomic human BSSL/CEL gene or an analogue thereof.

The mammary gland as a tissue of expression and genes encoding milk proteins are generally considered to be particularly suitable for use in the production of heterologous proteins in transgenic non-human mammals as milk proteins are naturally produced at high expression levels in the mammary gland. Also, milk is readily collected and available in large quantities. In the present connection the use of milk protein genes in the production of recombinant human BSSL/CEL has the further advantage that it is produced under conditions similar to the its natural production conditions in terms of regulation of expression and production location (the mammary gland).

In the present context the term "hybrid gene" denotes a DNA sequence comprising on the one hand a DNA sequence encoding human BSSL/CEL as defined above and on the other hand a DNA sequence of the milk protein gene which is capable of mediating the expression of the hybrid gene product. The term "gene encoding a milk protein" denotes an entire gene as well as a subsequence thereof capable of mediating and targeting the expression of the hybrid gene to the tissue of interest, i.e. the mammary gland. Normally, said subsequence is one which at least harbours one or more of a promoter region, a transcriptional start site, 3' and 5' non-coding regions and structural sequences. The DNA sequence encoding human BSSL/CEL is preferably substantially free from prokaryotic sequences, such as vector sequences, which may be associated with the DNA sequence after, e.g., cloning thereof.

The hybrid gene is preferably formed by inserting in vitro the DNA sequence encoding human BSSL/CEL into the milk protein gene by use of techniques known in the art. Alternatively, the DNA sequence encoding human BSSL/CEL can be inserted in vivo by homologous recombinantion.

Normally, the DNA sequence encoding human BSSL/CEL will be inserted in one of the first exons of the milk protein gene of choice or an effective subsequence thereof comprising the first exons and preferably a substantial part of the 5' flanking sequence which is believed to be of regulatory importance.

The hybrid gene preferably comprises a sequence encoding a signal peptide so as to enable the hybrid gene product to be secreted correctly into the mammary gland. The signal peptide will typically be the one normally found in the milk protein gene in question or one associated with the DNA sequence encoding human BSSL/CEL. However, also other signal sequences capable of mediating the secretion of the hybrid gene product to the mammary gland are relevant. Of course, the various elements of the hybrid gene should be fused in such a manner as to allow for correct expression and processing of the gene product. Thus, normally the DNA sequence encoding the signal peptide of choice should be precisely fused to the N-terminal part of the DNA sequence encoding human BSSL/CEL. In the hybrid gene, the DNA sequence encoding human BSSL/CEL will normally comprise its stop codon, but not its own message cleavance and polyadenylation site. Downstream of the DNA sequence encoding human BSSL/CEL, the mRNA processing sequences of the milk protein gene will normally be retained.

A number of factors are contemplated to be responsible for the actual expression level of a particular hybrid gene. The capability of the promoter as well of other regulatory sequences as mentioned above, the integration site of the expression system in the genome of the mammal, the integration site of the DNA sequence encoding human BSSL/CEL in the milk protein encoding gene, elements conferring post-transcriptional regulation and other similar factors may be of vital importance for the expression level obtained. On the basis of the knowledge of the various factors influencing the expression level of the hybrid gene, the person skilled in the art would know how to design an expression system useful for the present purpose.

A variety of different milk proteins are secreted by the mammary gland. Two main groups of milk proteins exist, namely the caseins and the whey proteins. The composition of milk from different species varies qualitatively as well as quantitatively with respect to these proteins. Most non-human mammals produces 3 different types of casein, namely α-casein, β-casein and κ-casein. The most common bovine whey proteins are α-lactalbumin and β-lactalbumin. The composition of milk of various origins are further disclosed in Clark et al. (1987).

The milk protein gene to be used may be derived from the same species as the one in which the expression system is to be inserted, or it may be derived from another species. In this connection it has been shown that the regulatory elements that target gene expression to the mammary gland are functional across species boundaries, which may be due to a possible common ancestor (Hennighausen et al., 1990).

Examples of suitable genes encoding a milk protein or effective subsequences thereof to be used in the construction of an expression system of the invention are normally found among whey proteins of various mammalian origins, e.g. a whey acidic protein (WAP) gene, preferably of murine origin, and a β-lactoglobulin gene, preferably of ovine origin. Also casein genes of various origins may be found to be suitable for the transgenic production of human BSSL/CEL, e.g. bovine αS1-casein and rabbit β-casein. The presently preferred gene is a murine WAP gene as this has been found to be capable of providing a high level of expression of a number of foreign human proteins in milk of different transgenic animals (Hennighausen et al, 1990).

Another sequence preferably associated with the expression system of the invention is a so-called expression stabilizing sequence capable of mediating high-level expression. Strong indications exist that such stabilizing sequences are found in the vicinity of and upstreams of milk protein genes.

The DNA sequence encoding human BSSL/CEL to be inserted in the expression system of the invention may be of genomic or synthetic origin or any combination thereof. Some expression systems have been found to require the presence of introns and other regulatory regions in order to obtain a satisfactory expression (Hennighausen et al., 1990). In some cases it may be advantageous to introduce genomic structures, rather than cDNA elements, as polypeptide encoding element in vector constructs (Brinster et al.). The intron and exon structure may result in higher steady state mRNA levels that obtained when cDNA based vectors are used.

In a further aspect, the present invention relates to a hybrid gene comprising a DNA sequence encoding human BSSL/CEL inserted into a gene encoding a milk protein of a non-human mammal, the DNA sequence being inserted in the milk protein gene in such a manner that it is expressible in the mammary gland of an adult female of a mammal harbouring the hybrid gene. The hybrid gene and its constituents have been discussed in detail above. The hybrid gene constitutes an important intermediate in the construction of an expression system of the invention as disclosed above.

In another aspect, the present invention relates to a non-human mammalian cell harbouring an expression system as defined above. The mammalian cell is preferably an embryo cell or a pro-nucleus. The expression system is suitably inserted in the mammalian cell using a method as explained in the following and specifically illustrated in the Example below.

In a further important aspect, the present invention relates to a method of producing a transgenic non-human mammal capable of expressing human BSSL/CEL, comprising injecting an expression system of the invention as defined above into a fertilized egg or a cell of an embryo of a mammal so as to incorporate the expression system into the germline of the mammal and developing the resulting injected fertilized egg or embryo into an adult female mammal.

The incorporation of the expression system into the germline of the mammal may be performed using any suitable technique, e.g. as described in "Manipulating the Mouse Embryo"; A Laboratory Manual, Cold Spring Harbor Laboratory Press, 1986. For instance, a few hundred molecules of the expression system may be directly injected into a fertilized egg, e.g. a fertilized one cell egg or a pro-nucleus thereof, or an embryo of the mammal of choice and the microinjected eggs may then subsequently be transferred into the oviducts of pseudopregnant foster mothers and allowed to develop. Normally, not all of the injected eggs will develop into adult females expressing human BSSL/CEL. Thus, about half of the mammals will from a statistically point of view be males from which, however, females can be bred in the following generations. Once integrated in the germ line, the DNA sequence encoding human BSSL/CSL may be expressed at high levels to produce a correctly processed and functional human BSSL/CEL in stable lines of the mammal in question.

Of further interest is a method of producing a transgenic non-human mammal capable of expressing human BSSL/CEL and substantially incapable of expressing BSSL/CEL from the mammal itself, comprising (a) destroying the mammalian BSSL/CEL expressing capability of the mamma% so that substantially no mammalian BSSL/CEL is expressed and inserting an expression system of the invention as defined above or a DNA sequence encoding human BSSL/CEL into the germline of the mammal in such a manner that human BSSL/CSL is expressed in the mammal; and/or (b) replacing the mammalian BSSL/CEL gene or part thereof with an expression system of the invention as defined above or a DNA sequence encoding human BSSL/CEL.

The mammalian BSSL/CEL expressing capability is conveniently destroyed by introduction of mutations in the DNA sequence responsible for the expression of the BSSL/CEL. Such mutations may comprise mutations which make the DNA sequence out of frame, or introduction of a stop codon or a deletion of one or more nucleotides of the DNA sequence.

The mammalian BSSL/CEL gene or a part thereof may be replaced with an expression system as defined above or a DNA sequence encoding human BSSL/CEL by use of the well known principles of homologous recombination.

In a further aspect, the present invention relates to a transgenic non-human mammal prepared by a method as described above.

While the transgenic non-human mammal of the invention in its broadest aspect is not restricted to any particular type of mammal, the mammal will normally be selected from the group consisting of mice, rats, rabbits, sheep, pigs, goats and cattle. For large scale production of human BSSL/CEL the larger animals such as sheep, goats, pigs and especially cattle are normally preferred due to their high milk production. However, also mice, rabbits and rats may be interesting due to the fact that the manipulation of these animals is more simple and results in transgenic animals more quickly than when, e.g. cattle, are concerned.

Also progeny of a transgenic mammal as defined above, capable of producing human BSSL/CEL is within the scope of the present invention.

In a further aspect the present invention includes milk from a non-human mammal comprising recombinant human BSSL/CEL.

In a still further aspect, the present invention relates to an infant formula comprising recombinant human BSSL/CEL, in particular a polypeptide of the invention as defined above. The infant formula may be prepared by adding the recombinant human BSSL/CEL or polypeptide in a purified or partly purified form to the normal constituents of the infant formula. However, normally it is preferred that the infant formula is prepared from milk of the invention as defined above, especially when it is of bovine origin. The infant formula may be prepared using conventional procedures and contain any necessary additives such as minerals, vitamins etc.

EXAMPLES

Example 1

Genomic Organization, Sequence Analysis and Chromosomal Localization of the Cel Gene Standard molecular biology techniques were used (Maniatis et al., 1982; Ausubel et al., 1987; Sambrook et al., 1989) if nothing else is mentioned.

Isolation of Genomic Recombinants

Two different human genomic phage libraries, λDASH (Clonentech Laboratories Inc., Palo Alto, Calif., USA) and λEMBL-3 SP6/T7 (Stratagene, La Jolla, Calif., USA), were screened by plaque hybridization using various subcloned cDNA restriction fragments (Nilsson et al., 1990) as probes, labeled with [α-$^{32}$P]dCTP by the oligolabeling technique (Feinberg et al., 1983).

Mapping, Subcloning and Sequencing of Genomic Clones

Positive clones were digested with various restriction enzymes, electrophoresed on 1% agarose gels and then vacuumtransfered (Pharmacia LKB BTG, Uppsala, Sweden) to a nylon membrane. The membrane was hybridized with various cDNA probes. Restriction fragments, hybridizing with the probes, were isolated using the isotachophoreses method (Öfverstedt et al., 1984). Smaller fragments, <800 bp, were directly inserted into M13mp1S, M13mp19, M13BM20 or M13BM21 vectors and sequenced, using $E.$ $coli$ TG1 as host bacteria, whereas larger fragments were subcloned into pTZ18R or pTZ19R vectors, using $E.$ $coli$ DH5α as host bacteria, and further digested. (The plasmids pS309, pS310 and pS451 used in Example 2 below were produced accordingly.) Some of the isolated fragments were also used as probes in hybridizations. All of the nucleotide sequence was determined by the dideoxy chain termination method (Sanger et al., 1977) using Klenow enzyme and either the M13 universal sequencing primer of specific oligonucleotides. Sequence information was retrieved from autoradiograms by the use of the software MS-EdSeq as described by Sjöberg et alo (1989). The sequences were analyzed using the programs obtained from the UWGCG software package (Devereux et al., 1984).

Primer Extension

Total RNA was isolated from human pancreas, lactating mammary gland and adipose tissue by the guanidinium isothiocyanate-CsCl procedure (Chirgwin et al., 1979). Primer extension was performed according to (Ausubel et al., 1987) using total RNA and an antisense 26-mer oligonucleotide (5'-AGGTGAGGCCCAACACAACCAGTTGC-3', SEQ ID NO: 2 in the Sequence Listing), nt position 33–58. Hybridization of the primer with 20 µg of the total RNA was performed in 30 µl of 0.9M NaCl, 0.15M Hepes pH 7.5 and 0.3M EDTA at 30° C. overnight. After the extension reaction with reverse transcriptase, the extension products were analyzed by electrophoresis through a 6% denaturing polyacrylamide gel.

Somatic Cell Hybrids

DNA from 16 human-rodent somatic cell hybrid lines, obtained from NIGMS Human Genetic Mutant Cell Repository (Coriell Institute for Medical Research, Camden, N.J.) were used for the chromosomal assignment of the CEL gene. Human-mouse somatic cell hybrids GM09925 through GM09940 were derived from fusions of fetal human male fibroblasts (IMR-91), with the thymidine kinase deficient mouse cell line B-82 (Taggart et al., 1985; Mohandas et al., 1986). Hybrids GM10324 and GM02860 with the HPRT and APRT deficient mouse cell line A9 (Callen et al., 1986), while hybrid GM10611 resulted from a microcell fusion of the retroviral vector SP-1 infected human lymphoblast cell line GM07890 with the Chinese hamster ovary line UV-135 (Warburton et al., 1990). Hybrid GM10095 was derived from the fusion of lymphocytes from a female with a balanced 46,X,t(X;9)(q13;34) karyotype with the Chinese hamster cell line CHW1102 (Mohandas et al., 1979). The human chromosome content of the hybrid lines, which was determined by cytogenetic analysis as well as by Southern blot analysis and in situ hybridization analysis, are shown in Table 1. High molecular weight DNAs isolated from mouse, Chinese hamster and human parental cell line and the 16 hybrid cell lines were digested with EcoRI, fractionated in 0.8% agarose gels, and transferred to nylon filters. A [α-$^{32}$P] dCTP-labeled CEL cDNA probe (a full-length cDNA) was prepared by oligolabeling (Feinberg and Vogelstein, 1983) and hybridized to the filters. The filters were washed for 60 min each at 65° C. in 6×SSC/0.5%SDS and in 2×SSC/0.5%SDS.

Polymerase Chain Reaction

Total human genomic DNA isolated from leukocytes, DNA from somatic cell hybrids and from some of the positive genomic recombinants and total RNA from human lactating mammary gland and human pancreas were amplified for exon 10 and exon 11. Two µg of DNA were used. The primers used are listed in Table 2 (SEQ ID NOS: 6–11). Thirty cycles of PCR were performed in 100 µl volume [10 mM Tris-HCl, pH 8.3, 50 mM KCl, 1.5 mM MgCl$_2$, 200 µM of each dNTP, 100 µg/ml gelatin, 100 pmol of each primer, 1.5 U Taq DNA polymerase (Perkin-Elmer Cetus, Norwalk, Conn., USA)] and the annealing temperature 55° C. for all the primer pairs. The RNA sequence was amplified by the use of combined complementary DNA (cDNA) and PCR methodologies. cDNA was synthesized from 10µg total RNA in 40 µl of a solution containing 50 mM Tris-HCl, pH 8.3, 50 mM KCl, 10 mM MgCl$_2$, 10 µg/ml BSA, 1 mM of each dNTP, 500 ng of oligo(dT)$_{12-18}$, 40 U ribonuclease inhibitor, and 200 U reverse transcriptase (MoMuLV), (BRL, Bethesda Research Laboratories, N.Y., USA) for 30 min at 42° C. The cDNA was precipitated and resuspended in 25 µl H$_2$O; 2 µl of this was amplified, as described above. The amplified fragments were analyzed on a 2% agarose gel. Some of the fragments were further subcloned and sequenced.

Gene Structure of the Human CEL Gene

In each genomic library, 10$^6$ recombinants were screened and the screenings yielded several positive clones, which were all isolated and mapped. Two clones, designated λBSSL1 and λBSSL5A, were further analyzed. Restriction enzyme digestions with several enzymes, Southern blotting followed by hybridization with cDNA probes, indicated that the λBSSL5A clone covers the whole CEL gene and that the λBSSL1 clone covers the 5'-half and about 10 kb of 5'-flanking region (FIG. 1). Together these two clones cover about 25 kb of human genome.

After subcloning and restriction enzyme digestion, suitable fragments for sequencing were obtained and the entire sequence of the CEL gene could be determined, including 1640 bp of the 5'-flanking region and 41 bp of the 3'-flanking region. These data revealed that the human CEL gene (SEQ ID NO: 1) span a region of 9850 bp, containing 11 exons interrupted by 10 introns (FIG. 1). This means that the exons and especially the introns are relatively small. In fact, exons 1–10 range in sizes from 87–204 bp respectively while exon 11 is 841 bp long. The introns range in sizes from 85–2343 bp respectively. As can be noted in Table 3 (SEQ ID NOS: 12–31), all exon/intron boundaries obey the AG/GT rule and conform well to the consensus sequence suggested by Mount et al. (1982). When the coding part of the CEL gene was compared with the cDNA (Nilsson et al., 1990), only one difference in nucleotide sequence was found; the second nt in exon 1, a C, which in the cDNA sequence is a T. Since this position is located 10 nt upstream the translation start codon ATG, this difference does not influence the amino acid sequence.

Seven members of the Alu class of repetitive DNA elements are present in the sequenced region, labeled Alu1-Alu7(B'-3')(FIG. 1), one in the 5'-flanking region and the six others within the CEL gene.

Transcription Initiation Sites and 5'-Flanking region

Figure 2:
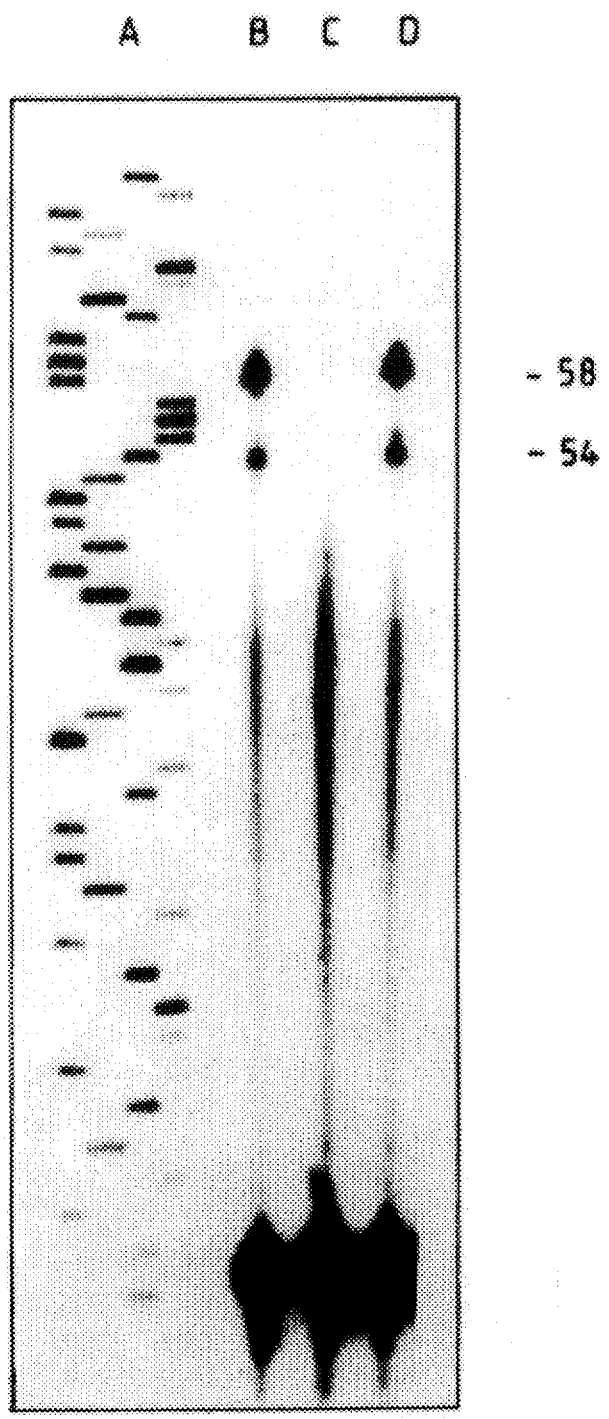
Figure 3:
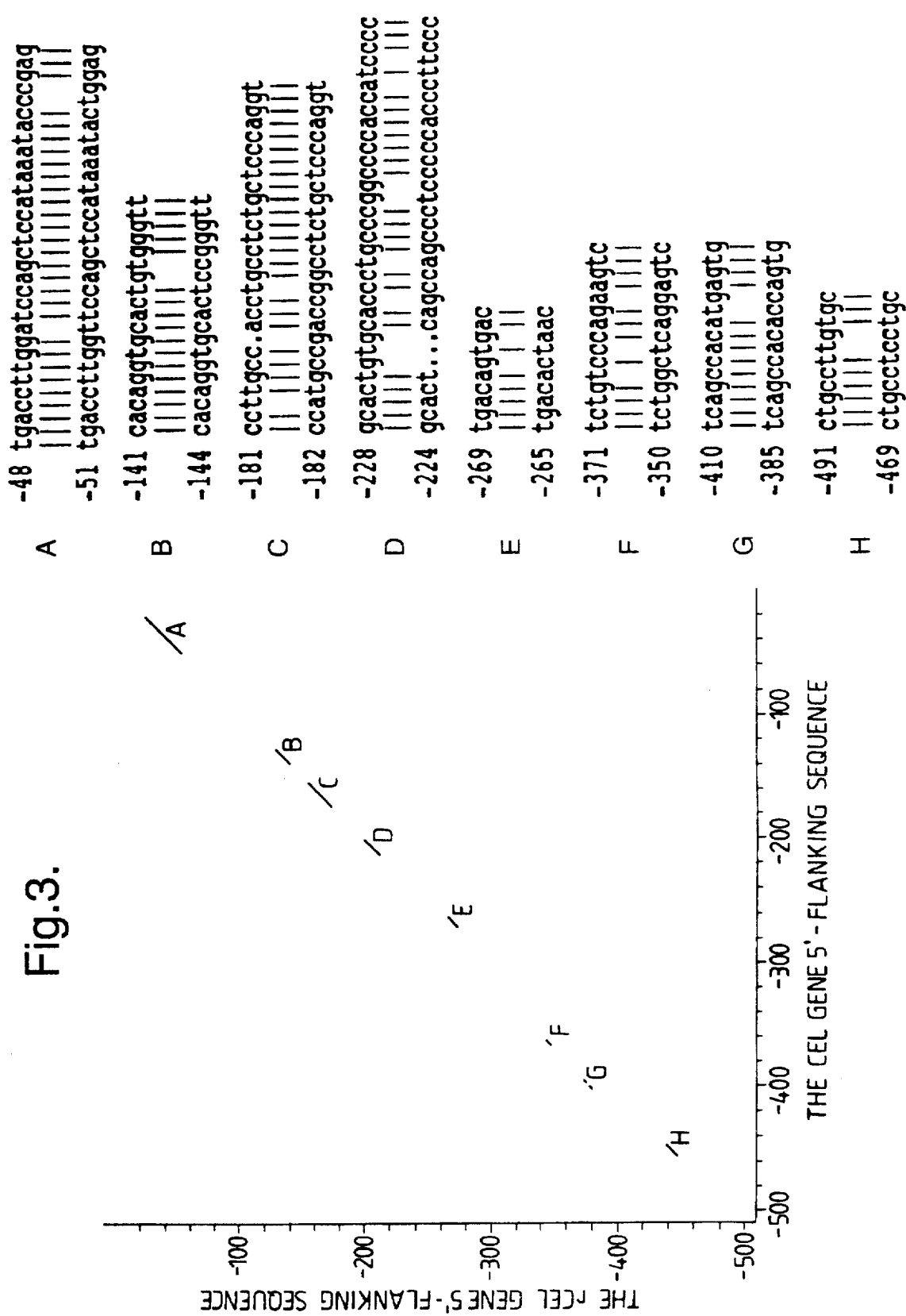

To map the human CEL gene transcription initiation site(s), primer extension analysis was performed using total RNA from human pancreas, lactating mammary gland and adipose tissue. The results indicated a major transcription start site located 12 bp, and a minor start site located 8 bases, upstream of the initiator methionine. The transcription initiation sites are the same in both pancreas and lactating mammary gland whereas no signal could be detected in adipose tissue (FIG. 2). The sequenced region includes 1640 nt of 5'-flanking DNA. Based on sequence similarities a TATA-box-like sequence, CATAAAT was found 30 nt upstream the transcription initiation site (FIG. 4, SEQ ID NO: 32 in the Sequence Listing). Neither a CAAT-box structure nor GC boxes were evident in this region.

The 5'-flanking sequence was computer screened, in both strands, for nucleotide sequences known as transcription factor binding sequences in other mammary gland- and pancreatic-specific genes. Several putative recognition sequences were found, see FIG. 4.

Chromosomal Localization of the CEL Gene

In human control DNA the CEL cDNA probe detected four EcoRI fragments of approximately 13 kb, 10 kb, 2.2 kb and 2.0 kb, while in the mouse and hamster control DNAs single fragments of about 25 kb and 8.6 kb, respectively, were detected. The presence of human CEL gene sequences in the hybrid clones correlated only with the presence of human chromosome 9 (Table 1). Only one of the 16 hybrids analyzed were positive for the human CEL gene; this hybrid contained chromosome 9 as the only human chromosome. No discordancies for localization to this chromosome were found, whereas there were at least two discordancies for localization to any other chromosome (Table 1). To further sublocalize the CEL gene we utilized a human-Chinese hamster hybrid (GM 10095) retaining a der(9) translocation chromosome (9pter→9g34:Xq13→Xgter) as the only human DNA. By Southern blot we failed to detect any CEL gene sequences in this hybrid, indicating that the CEL gene resides within the 9g34-qter region.

Example 2

Construction of Expression Vectors

Figure 5A:
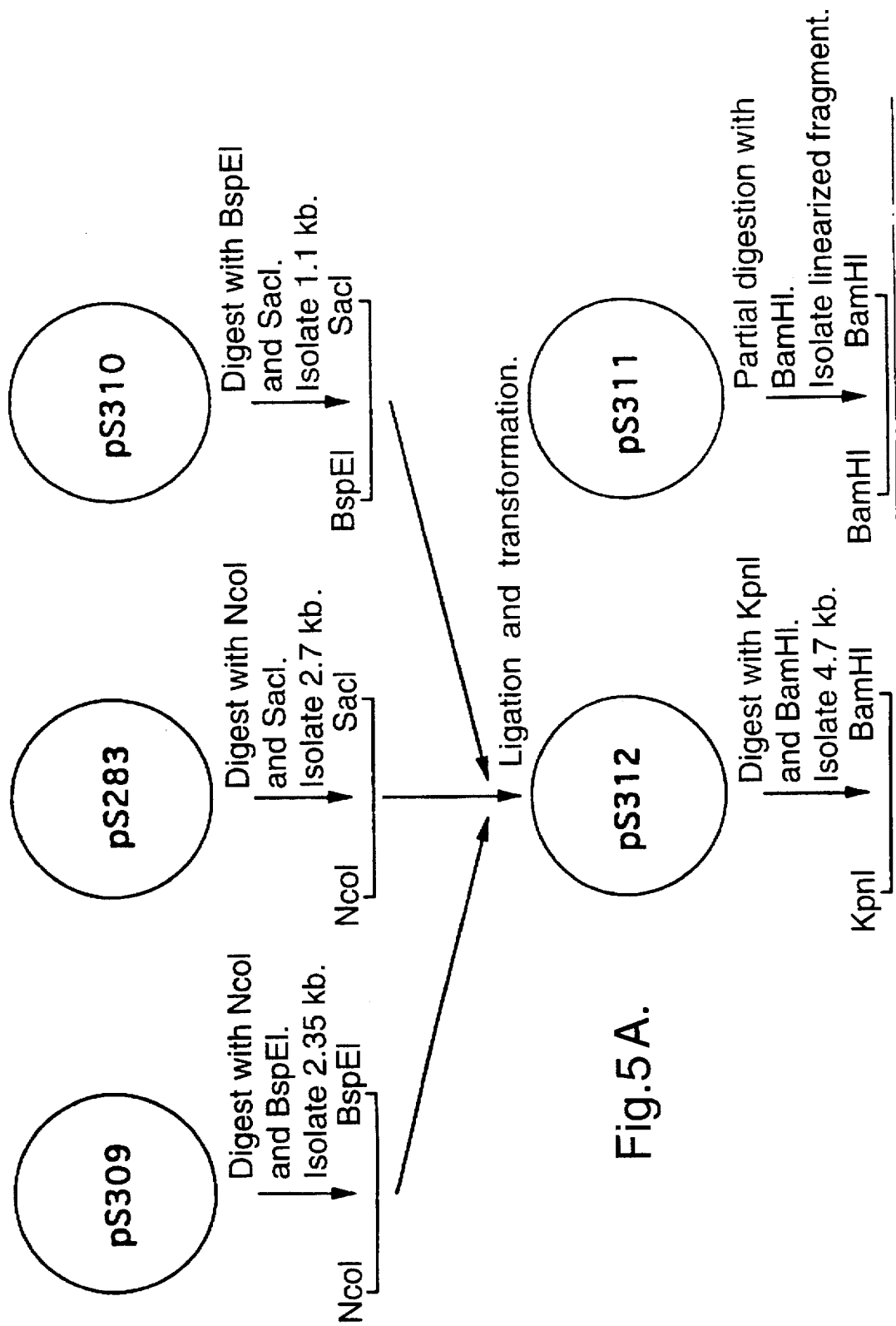
Figure 5B:
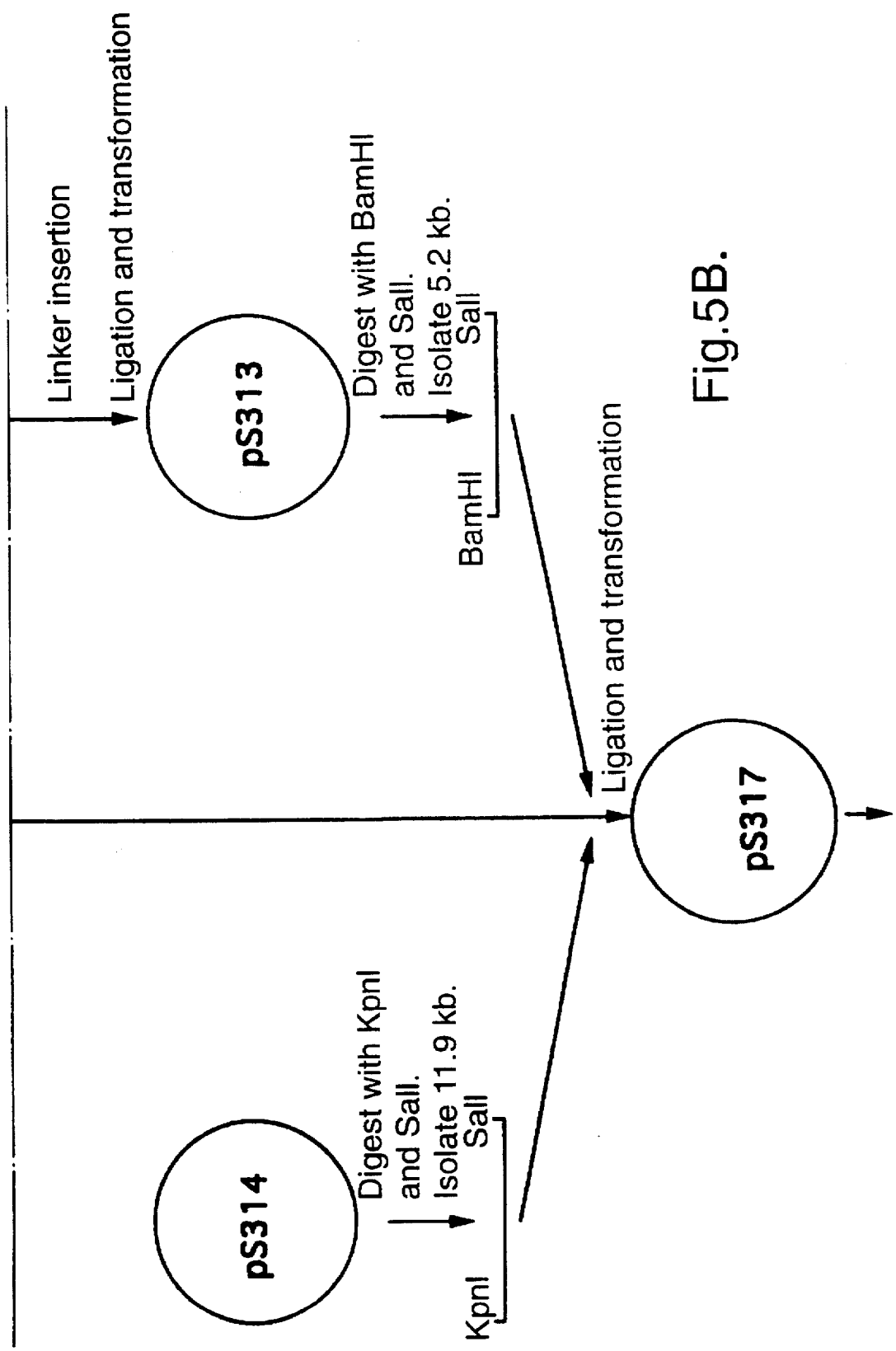
Figure 5C:
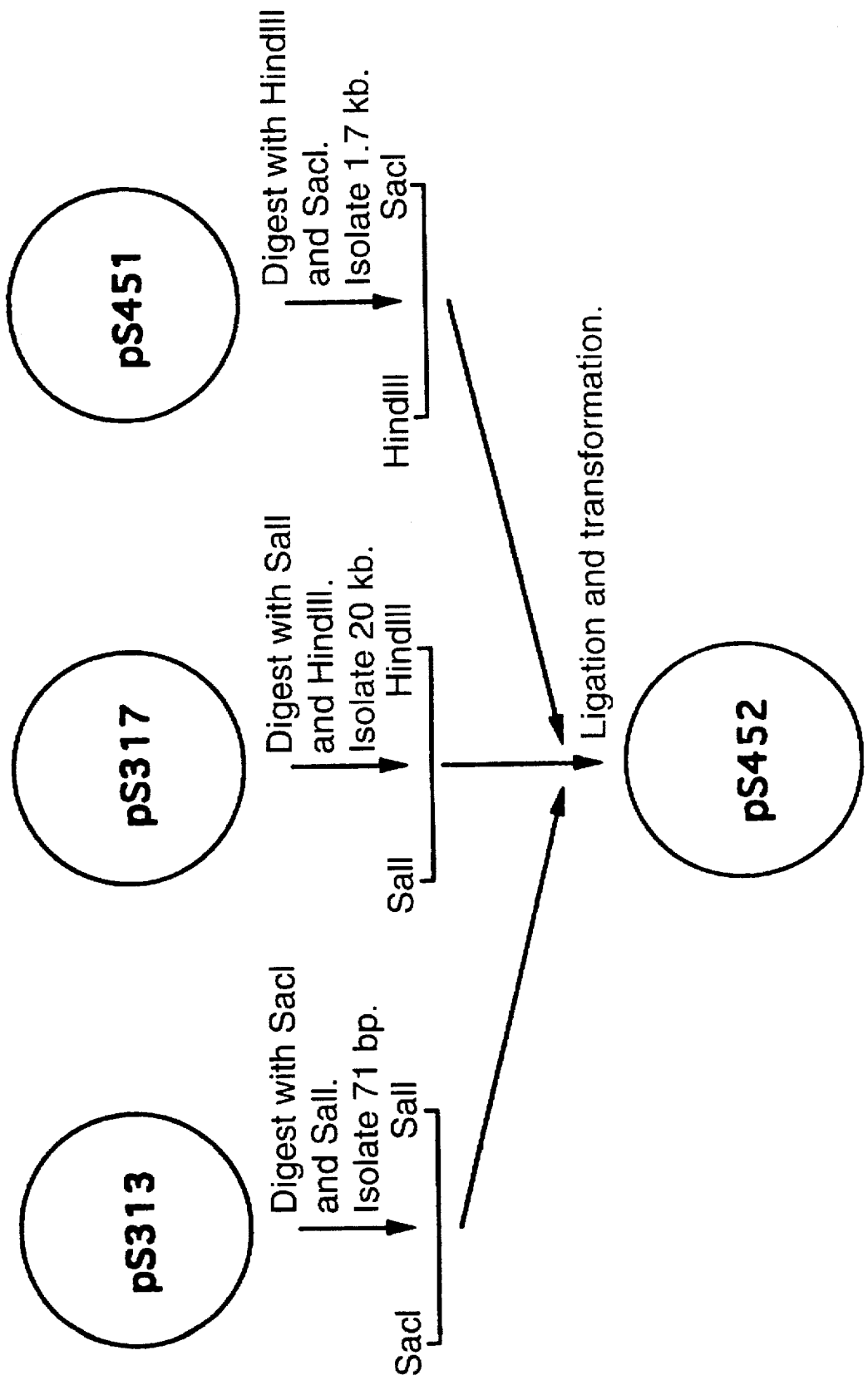

To construct an expression vector for production of recombinant human CEL in milk from transgenic animals the following strategy was employed (FIG. 5).

Three pTZ based plasmids (Pharmacia, Uppsala, Sweden) containing different parts of the human CEL gene, pS309, pS310 and pS311 were obtained using the methods described above. The plasmid pS309 contains a SphI fragment covering the the CEL gene from the 5' untranscribed region to part of the fourth intron. The plasmid pS310 contains a SacI fragment covering the CEL gene sequence from part of the first intron to a part of the sixth intron. Third, the plasmid pS311 contains a BamHI fragment covering a variant of the CEL gene from a major part of the fifth intron and the rest of the intron/exon structure. In this plasmid, the repetitive sequence of exon 11 that normally encodes the 16 repeats was mutated to encode a truncated variant having 9 repeats.

Figure 6:
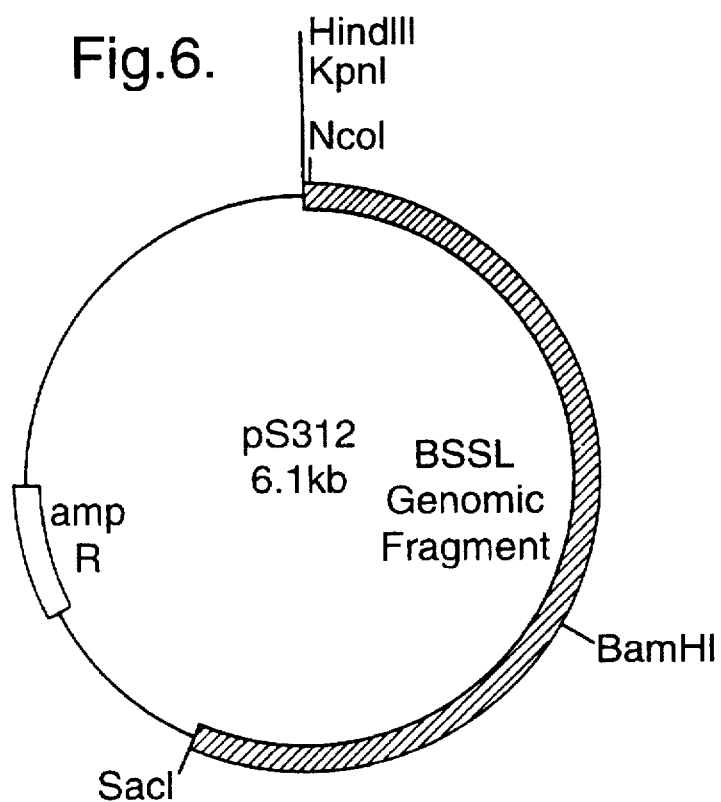

Another plasmid, pS283, containing a part of the human CEL cDNA cloned into the plasmid pUC19 at the HindIII and SacI sites was used for fusion of the genomic sequences. pS283 was also used to get a convenient restriction enzyme site, KpnI, located in the 5' untranslated leader sequence of CEL. Plasmid pS283 was then digested with NcoI and SacI and a fragment of about 2.7 kb was isolated. Plasmid pS309 was digested with NcoI and BspEI and a fragment of about 2.3 kb containing the 5'-part of the CEL gene was isolated. Plasmid pS310 was digested with BspEI and SacI and a fragment of about 2.7 kb containing a part of the middle region of the CEL gene was isolated. These three fragments were ligated and transformed into competent E. coli, strain TG2, and transformants were isolated by ampicillin selection. Plasmids were prepared from a number of transformants, and one plasmid called pS312 (FIG. 6), containing the desired construct was used for further experiments.

To obtain a modification of pS311, in which the BamHI site located downstream of the stop codon was converted to a SalI site to facilitate further cloning, the following method was used. pS311 was linearized by partial BamHI digestion. The linearized fragment was isolated and a synthetic DNA linker that converts BamHI to a SalI site (5'-GATCGTCGAC-3', SEQ ID NO: 3 in the Sequence Listing), thereby destroying the BamHI site, was inserted. Since there were two potential positions for integration of the synthetic linker the resulting plasmids were analyzed by restriction enzyme cleavage. A plasmid with the linker inserted at the desired position downstream of exon 11 was isolated and designated pS313.

To obtain the expression vector construct that harbours CEL genomic sequences and encodes the truncated CEL variant, the plasmid pS314 which was designed to mediate stage and tissue specific expression in the mammary gland cells under lactation periods was used. Plasmid pS314 contains a genomic fragment from the murine whey acidic protein (WAP) gene (Campbell et al. 1984) cloned as a NotI fragment. The genomic fragment has approximately 4.5 kb upstream regulatory sequences (URS), the entire transcribed exon/intron region and about 3 kb of sequence downstream of the last exon. A unique KpnI site is located in the first exon 24 bp upstream of the natural WAP translation initiation codon. Another unique restriction enzyme site is the SalI site located in exon 3. In pS314, this SalI site was destroyed by digestion, fill in using Klenow and religation. Instead, a new SalI site was introduced directly downstream of the KpnI site in exon 1. This was performed by KpnI digestion and introduction of annealed synthetic oligomers SYM 2401 5'-CGTCGACGTAC-3'(SEQ ID NO: 4 in the Sequence Listing), and SYM 2402 5'-GTCGACGGTAC-3' (SEQ ID NO: 5 in the Sequence Listing), at this position (FIG. 8) The human CEL genomic sequence was inserted between these sites, KpnI and SalI, by the following strategy. First, pS314 was digested with KpnI and SalI and a fragment representing the cleaved plasmid was electrophoretically isolated. Second, pS312 was digested with KpnI and BamHI and a approximately 4.7 kb fragment representing the 5'part of the human CEL gene was isolated. Third, pS313 was digested with BamHI and SalI and the 3'-part of the human CEL gene was isolated. These three fragments were ligated, transformed into competent E. coli bacteria and transformants were isolated after ampicillin selection. Plasmids were prepared from several transformants and carefully analyzed by restriction enzyme mapping and sequence analysis. One plasmid representing the desired expression vector was defined and designated pS317.

Figure 7:
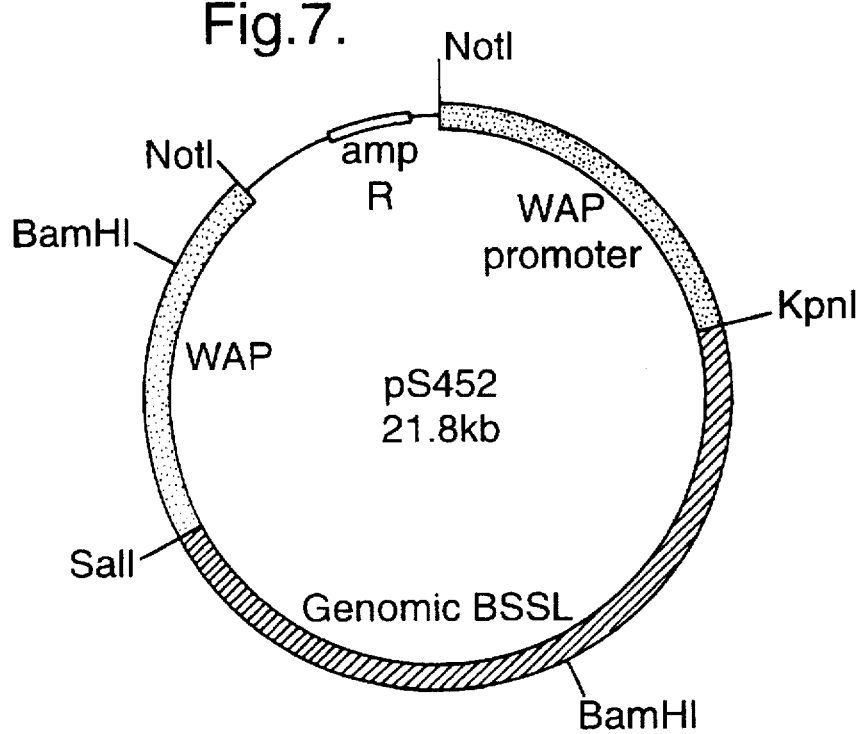

In order to construct a genomic CEL expression vector encoding full-length CEL pS317 was modified as follows (FIG. 5). First, a pTZ18R plasmid (Pharmacia) containing a 5.2 kb BamHI fragment of the human CEL gene extending from the fifth intron to downstream of the eleventh exon, pS451, was digested with HindIII and SacI. This digestion generated a fragment of about 1.7 kb that extends from the HindIII site located in intron 9 to the SacI site located in exon 11. Second, the plasmid pS313 was digested with SacI and SalI, and a 71 bp fragment containing the 3'part of exon 11 and the generated SalI site was isolated. Third, the rest of the WAP/CEL recombinant gene and the plasmid sequences was isolated as a SalI/HindIII fragment of about 20 kb from pS317. These three fragments were ligated and transformed into bacteria. Plasmids were prepared from several transformants. The plasmids were digested with various restriction enzymes and subjected to sequence analysis. One plasmid containing the desired recombinant gene was identified. This final expression vector was designated pS452 (FIG. 7).

To remove the prokaryotic plasmid sequences, ps452 was digested with NotI. The recombinant vector element consisting of murine WAP sequence flanking the human CEL genomic fragment was then isolated by agarose electrophoresis. The isolated fragment was further purified using electroelution, before it was injected into mouse embryos.

Figure 8:
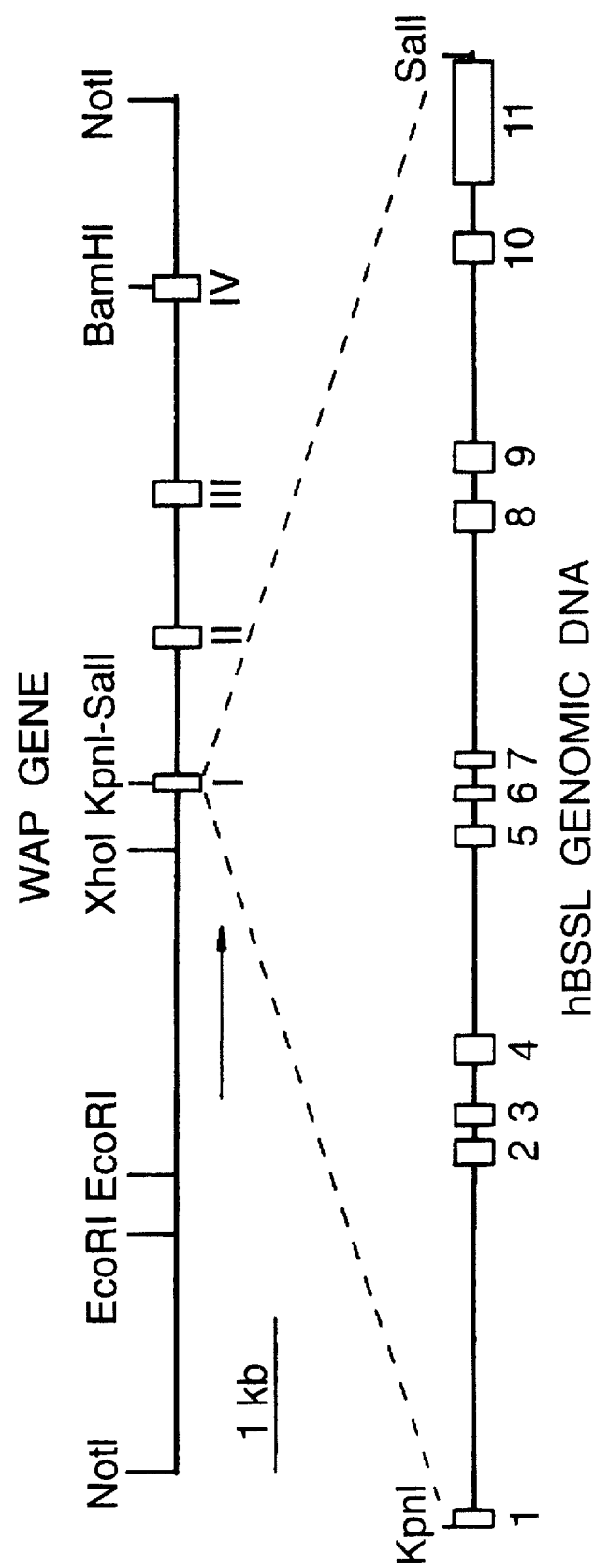

The recombinant WAP/CEL gene for expression in mammary gland of transgenic animals is shown in FIG. 8.

DEPOSITS

The following plasmids have been deposited in accordance with the Budapest Treaty at DSM (Deutsche Sammlung yon Mikroorganismen und Zellkulturen):

| Plasmid | Deposit No. | Date of deposit |
|---------|-------------|-----------------|
| pS309   | DSM 7101    | 12 June 1992    |
| pS310   | DSM 7102    |                 |
| pS451   | DSM 7498    | 26 February 1993 |
| pS452   | DSM 7499    |                 |

Example 3

Generation of Transgenic Animals

A NotI fragment was isolated from the plasmid pS452 according to Example 2. This DNA fragment contained the murine WAP promoter linked to a genomic sequence encoding human BSSL/CEL. The isolated fragment, at a concentration of 3 ng/µl, was injected into the pronucleus of 350 C57Bl/6JxCBA/2J-$f_2$ embryos obtained from donor mice primed with 5 IU pregnant mare's serum gonadotropin for superovulation. The C57Bl/6JxCBA/2J-$f_1$ animals were obtained from Bomholtgård Breeding and Research Centre LTD, Ry, Denmark. After collection of the embryos from the oviduct, they were separated from the cumulus cells by treatment with hyaluronidase in the medium M2 (Hogan et al., 1986). After washing the embryos were transferred to the medium M16 (Hogan et al., 1986) and kept in an incubator with 5% $CO_2$-atmosphere. The injections were performed in a microdrop of M2 under light paraffin oil using Narishigi hydraulic micromanipulators and a Nikon inverted microscope equipped with Nomarski optics. After injection, healthy looking embryos were implanted into pseudopregnant C57Bl/6JxCBA/2J-$f_1$ recipients given 0.37 ml of 2.5% Avertin intraperitoneally. Mice that had integrated the transgene were identified with PCR analysis of DNA from tail biopsy specimens obtained three weeks after birth of the animals. Positive results were confirmed with Southern blot analysis.

Example 4

Expression of BSSL/CEL in Transgenic Mice

Transgenic mice were identified by analysis of DNA which has been prepared from excised tail samples. The tissue samples were incubated with proteinase K and phenol/chloroform extracted. The isolated DNA was used in polymerase chain reactions with primers which amplify specific fragments if the heterologous introduced DNA representing the expression vector fragment is present. The animals were also analyzed by DNA hybridization experiments to confirm PCR data and to test for possible rearrangements, structure of the integrated vector elements and to obtain information about the copy number of integrated vector elements.

In one set of experiments, 18 mice were analyzed with the two methods and the results demonstrated that 1 mouse was carrying the heterologous DNA vector element derived from ps452. The result from the PCR analysis and the hybridization experiments were identical (FIG. 9) SEQ ID NOS: 57 and 58 in the Sequence Listing.

The mouse identified to carry vector DNA element (founder animal) was then mated and the F1 litter was analyzed for transgene by the same procedures.

Female lactating animals were injected with 2 IU oxytocin intraperitoneally and 10 minutes later anaesthetized with 0.40 ml of 2.5% Avertin intraperitoneally. A milk collecting device was attached to the nipple via a siliconized tubing and milk was collected into a 1.5 ml Eppendorf tube by gentle massage of the mammary gland. The amount of milk varied, dependent on the day of lactation, between 0.01 and 0.5 ml per mouse and collection.

Figure 10:
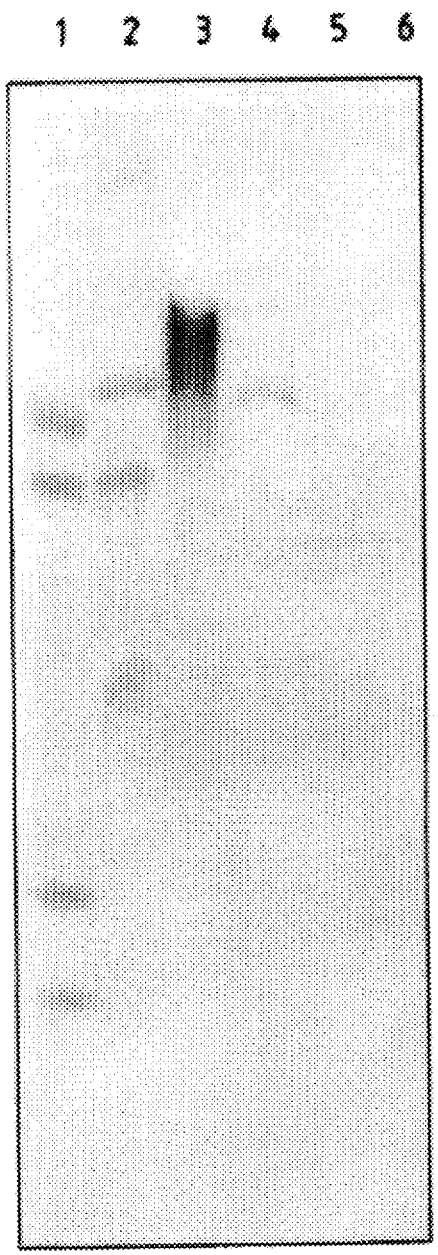

Analyze for the presence of recombinant human BSSL/CEL was done by SDS-PAGE, transfer to nitrocellulose membranes and incubation with polyclonal antibodies generated against native human BSSL/CEL. The obtained results demonstrated expression of recombinant human BSSL/CEL in milk from transgenic mice. FIG. 10 demonstrates presence of recombinant human BSSL/CEL in milk from transgenic mice: the band at about 116.5.

Stable lines of transgenic animals are generated.

In a similar manner, other transgenic animals such as cows or sheep capable of expressing human BSSL/CEL may be prepared.

REFERENCES

Abouakil, N., Rogalska, E., Bonicel, J. & Lombardo, D. (1988): Biochim. Biophys. Acta 961, 299–308.

Ausubel, F. M., Brent, R. E., Moore, D. D., Smiyh, J. A., Seidman, J. G. and Struhl, K.: Current Protocols in Molecular Biology. (Wiley Interscience, New York 1987)

Baba, T., Downs, D., Jackson, K. W., Tang, J. and Wang, C. S. (1991): Biochemistry 30, 500–510.

Beato, M. (1989): Cell 56, 335–344.

Bernbäck, S., Bläckberg, L. & Hernell, O. (1990): J. Clin. Invest. 221–226.

Björksten, B., Burman, L. G., deChateau, P., Fredrikzon, B., Gothefors, L. & Hernell, O. (1980): Br. Med. J. 201, 267–272.

Bläckberg, L., Ångquist, K. A, & Hernell, O. (1987): FEBS Lett. 217, 37–41.

Bläckberg, L. & Hernell, O. (1981): Eur. J. Biochem 116, 221–225.

Bläckberg, L. Lombardo, D., Hernell, O., Guy, O. & Olivecrona, T. (1981): FEBS Lett. 136, 284–288.

Boulet, A. M., Erwin, C. R. and Rutter, W. J. (1986): Proc. Natl. Acad. Sci. U.S.A. 83, 3599–3603.

Brinster, R. L., Allen, J. M., Behringer, R. R., Gelinas, R. E. & Palmiter, R. D. (1988): Proc. Natl. Acad. Sci. U.S.A. 85, 836–840.

Callen, D. F. (1986): Ann. Genet. 29, 235–239.

Campbell, S. M., Rosen, J. M., Hennighausen, L. G., Strech-Jurk, U. and Sippel, A. E. (1984): Nucleic Acid Res. 12, 8685–8697.

Chirgwin, J. M., Przybyla, A. E., MacDonald, R. J. and Rutter, W. J. (1979): Biochemistry 18, 5294–5299.

Clark, A. J., Simons, P., Wilmut, I. and Lahte, R. (1987): TIBTECH 5, 20–24.

Devereux, J., Haeberli, P. and Smithies. (1984): Nucleic Acids Res. 12, 387–395.

Feinberg, A. and Vogelstein, B. (1983): Anal. Biochem. 132, 6–13.

Hennighausen, L., Ruiz, L. & Wall, R. (1990): Current Opinion in Biotechnology 1, 74–78.

Hernell, O. & Bläckberg, L. (1982): Pediatr. Res. 16, 882–885.

Hogan, B., Constantini, F. and Lacy, E. (1986): Manipulating the mouse embryo. A Laboratory Manual. Cold Spring Harbor Laboratory Press.

Hui, D. and Kissel, J. A. (1990): Febs Lett. 276, 131–134.

Lombardo, D., Guy, O. & Figarella, C. (1978): Biochim. Biophys. Acta 527, 142–149.

Maniatis, T., Fritsch, E. F. & Sambrook, J.: Molecular Cloning. A Laboratory Manual. (Cold Spring Harbor, N.Y., 1982)

Mohandas, T., Sparkes, R. S., Sparkes, M. C., Shulkin, J. D., Toomey, K. E. and Funderburk, S. J. (1979): Am. J. Hum. Genet. 31, 586–600.

Mohandas, T., Heinzmann, C., Sparkes, R. S. Wasmuth, J., Edwards, P. and Lusis, A. J. (1986): Somatic Cell. Mol. Genet. 12, 89–94.

Mount, S. M. (1982): Nucleic Acids Res. 10, 459–472.

Nilsson, J., Bläckberg, L., Carlsson, P., Enerbäck, S., Hernell, O. and Bjursell, G. (1990): Eur. J. Biochem. 192, 543–550.

Qasba, M., and Safaya, S. K. (1984): Nature 308, 377–380.

Reue, K., Zambaux, J., Wong, H., Lee, G., Leete, T. H., Ronk, M., Shively, J. E., Sternby, B., Borgström, B., Ameis, D. and Schotz, M. C. (1991): J. Lipid. Res. 32, 267–276.

Sambrook, J., Fritsch, E. F. and Maniatis, T. E.: Molecular Cloning. A Laboratory Manual. (Cold Spring Harbor, N.Y., 1989)

Sanger, F., Nicklen, S. and Coutson, A. R. (1977): Proc. Natl. Acad. Sci. U.S.A. 74, 5463–5467.

Sjöberg, S., Carlsson, P., Enerbäck, S. and Bjursell, G. (1989): Comput. Appl. Biol. Sci. 5,41–46.

Taggart, R. T., Mohandas, T., Shows, T. B. and Bell, G. I. (1985): Proc. Natl. Acad. Sci. U.S.A. 82, 6240–6244.

Warburton, D., Gersen, S., Yu, M. T., Jackson, C., Handelin, B. and Housman, D. (1990): Genomics 6, 358–366.

Whitelaw et al. (1991): Transgenic Research 1, 3–13.

Yu-Lee, L., Richter-Mann, L., Couch, C., Stewart, F., Mackinlay, G. and Rosen, J. (1986): Nucleic. Acid. Res. 14, 1883–1902.

Öfverstedt, L. G., Hammarström, K., Balgobin, N., Hjerten, S., Petterson, U. and Chattopadhyaya, J. (1984): Biochim. Biophys. Acta 782, 120–126.

TABLE 1

Correlation of CEL sequences with human chromosomes in 16 human-rodent somatic cell hybrids.

| CHROMOSOME | PERCENTAGE OF CELLS WITH HUMAN CHROMOSOMES[a] | | | | | | | | | | | | | | | | | | | | | | | | CEL |
|---|---|---|---|---|---|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | X | Y | |
| HYBRID | | | | | | | | | | | | | | | | | | | | | | | | | |
| GM09925 | 74 | 24 | 0 | 74 | 76 | 60 | 82 | 78 | 0 | 0 | 4 | 68 | 6 | 86 | 78 | 14 | 98 | 96 | 46 | 84 | 0 | 76 | 0 | 0 | − |
| GM09927 | 69 | 83 | 75 | 77 | 0 | 93 | 79 | 73 | 0 | 82 | 0 | 0 | 77 | 79 | 90 | 0 | 81 | 73 | 87 | 89 | 0 | 0 | 0 | 0 | − |
| GM09929 | 0 | 0 | 61 | 59 | 0 | 43 | 2 | 49 | 0 | 0 | 33 | 49 | 0 | 59 | 2 | 0 | 96 | 0 | 2 | 31 | 0 | 0 | 2 | 0 | − |
| GM09930A | 0 | 34 | 62 | 4 | 12 | 0 | 26 | 4 | 0 | 0 | 6 | 22 | 56 | 82 | 12 | 0 | 86 | 78 | 0 | 22 | 82 | 76 | 6 | 8 | − |
| GM09932 | 0 | 0 | 0 | 68 | 86 | 46 | 0 | 80 | 0 | 2 | 28 | 26 | 0 | 0 | 0 | 0 | 96 | 0 | 2 | 0 | 92 | 0 | 0 | 0 | − |
| GM09933 | 50 | 0 | 84 | 16 | 54 | 76 | 92 | 54 | 0 | 6 | 0 | 50 | 84 | 78 | 92 | 0 | 88 | 70 | 80 | 32 | 94 | 88 | 0 | 32 | − |
| GM09934 | 0 | 50 | 0 | 0 | 83 | 79 | 4 | 87 | 0 | 0 | 77 | 87 | 0 | 2 | 89 | 0 | 90 | 89 | 0 | 91 | 89 | 2 | 0 | 0 | − |
| GM09935A | 0 | 0 | 52 | 10 | 28 | 12 | 0 | 0 | 0 | 8 | 0 | 22 | 74 | 72 | 0 | 0 | 93 | 59 | 0 | 9 | 91 | 71 | 0 | 0 | − |
| GM09936 | 0 | 0 | 0 | 18 | 0 | 46 | 70 | 10 | 0 | 16 | 34 | 0 | 2 | 88 | 2 | 0 | 100 | 0 | 44 | 24 | 0 | 18 | 0 | 0 | − |
| GM09937 | 0 | 0 | 54 | 38 | 0 | 62 | 54 | 70 | 0 | 4 | 0 | 42 | 0 | 70 | 60 | 0 | 96 | 66 | 0 | 0 | 0 | 0 | 0 | 0 | − |
| GM09938 | 0 | 0 | 2 | 88 | 60 | 88 | 86 | 4 | 0 | 0 | 36 | 92 | 0 | 80 | 4 | 0 | 92 | 0 | 4 | 80 | 76 | 60 | 0 | 2 | − |
| GM09940 | 0 | 0 | 46 | 0 | 0 | 0 | 84 | 62 | 0 | 0 | 0 | 0 | 0 | 0 | 62 | 0 | 100 | 0 | 0 | 0 | 0 | 0 | 0 | 0 | − |
| GM10324 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 90 | 0 | − |
| GM10567 | 0 | 0 | 0 | 0 | 0 | 0 | 0 | 0 | 0 | 0 | 0 | 0 | 0 | 0 | 0 | 98 | 0 | 0 | 0 | 0 | 0 | 0 | 0 | 0 | − |
| GM10611 | 0 | 0 | 0 | 0 | 0 | 0 | 0 | 0 | 69 | 0 | 0 | 0 | 0 | 0 | 0 | 0 | 0 | 0 | 0 | 0 | 0 | 0 | 0 | 0 | + |
| GM10095 | 0 | 0 | 0 | 0 | 0 | 0 | 0 | 0 | 94[b] | 0 | 0 | 0 | 0 | 0 | 0 | 0 | 0 | 0 | 0 | 0 | 0 | 0 | 94[b] | 0 | − |
| Discordancy ratio | $\frac{4}{16}$ | $\frac{5}{16}$ | $\frac{8}{16}$ | $\frac{7}{16}$ | $\frac{7}{16}$ | $\frac{10}{16}$ | $\frac{9}{16}$ | $\frac{9}{16}$ | $\frac{0}{16}$ | $\frac{2}{16}$ | $\frac{6}{16}$ | $\frac{10}{16}$ | $\frac{5}{16}$ | $\frac{10}{16}$ | $\frac{7}{16}$ | $\frac{2}{16}$ | $\frac{13}{16}$ | $\frac{8}{16}$ | $\frac{5}{16}$ | $\frac{9}{16}$ | $\frac{7}{16}$ | $\frac{6}{16}$ | $\frac{3}{16}$ | $\frac{2}{16}$ | |

[a]In general, a human chromosome has to be present in more than 20 to 22% of the cells to be detected by Southern blot analysis
[b]Contains 9pter->q34 and Xq13->qter.

TABLE 2

Primers Used for DNA Amplification

| Oligonucleotide | nt Position[a] | Sequence amplified |
|---|---|---|
| P1: 5'-AGACCTACGCCTACCTG-3' | 8492–8508 | Exon 10 |
| P2: 5'-TCCAGTAGGCGATCATG-3' | 8646–8662 | |
| P4: 5'-GACCGATGTCCTCTTCCTGG-3' | 7220–7239 | Exon 10 with primers from |
| P5: 5'-CAGCCGAGTCGCCCATGTTG-3' | 9016–9035 | exons surrounding exon 10[b] |
| P6: 5'-ACCAAGAAGATGGGCAGCAGC-3' | 9089–9109 | The repetition in exon 11 |
| P7: 5'-GACTGCAGGCATCTGAGCTTC-3' | 9722–9742 | |

[a]The nucleotide position is given as the number of bases from the start of the first exon. In order to compare the nucleotide position with SEQ ID NO: 1, add 1640 bases to the number in the column.
[b]For amplification of "exon 10" from cDNA

TABLE 3

Exon-Intron organization of the CEL gene

| Exon | | | | | sequence at exon-intron junction | | Intron | |
|---|---|---|---|---|---|---|---|---|
| no. | nucleotide position[a] | length (nt) | amino acids pos. | no. | 5'splice donor | 3'splice acceptor | no. | length (nt) |
| 1  | 1–87      | 87  | 1–25    | (25)  | GCC GCG AAG  gtaaga ... gtgtctccctcgcag  CTG GGC GCC | | I    | 2343 |
| 2  | 2431–2581 | 151 | 26–75   | (50)  | TGG CAA G    gtggga ... tcctgccacctgcag  GG ACC CTG  | | II   | 85   |
| 3  | 2667–2789 | 123 | 76–116  | (41)  | AAG CAA G    gtctgc ... gctcccccatctcag  TC TCC CGG  | | III  | 277  |
| 4  | 3067–3264 | 198 | 117–182 | (66)  | CTG CCA G    gtgcgt ... ctgccctgcccccag  GT AAC TAT  | | IV   | 1288 |
| 5  | 4553–4683 | 131 | 183–226 | (44)  | TCT CTG CAG  gtctcg ... ttctgggtcccgtag  ACC CTC TCC | | V    | 177  |
| 6  | 4861–4968 | 108 | 227–262 | (36)  | GCC AAA AAG  gtaaac ... tggttctgcccccag  GTG GCT GAG | | VI   | 142  |
| 7  | 5111–5228 | 118 | 263–301 | (39)  | CTG GAG T    gtgagt ... ggctctcccacccag  AC CCC ATG  | | VII  | 1466 |
| 8  | 6695–6881 | 187 | 302–364 | (63)  | GTC ACG GA   gtaagc ... acttgattcccccag  G GAG GAC   | | VIII | 197  |
| 9  | 7079–7282 | 204 | 365–432 | (68)  | AAT GCC AA   gtgagg ... gtctctcccctccag  G AGT GCC   | | IX   | 1201 |
| 10 | 8484–8681 | 198 | 433–498 | (66)  | AAA ACA GG   gtaaga ... cttctcactctgcag  G GAC CCC   | | X    | 328  |
| 11 | 9010–9850 | 841 | 499–745 | (247) | | | | |

[a]The nucleotide position is given as the number of bases from the start of the first exon. In order to compare the nucleotide position with SEQ ID NO: 1, add 1640 bases to the number in the column.

---

I claim:

1. A process of producing a transgenic non-human female mammal that expresses recoverable amounts of biologically functional human BSSL/CEL in its milk, comprising:

(a) introducing an expression system into a fertilized egg of a non-human mammal; wherein
    (i) said expression system comprises a hybrid gene that is expressed in the mammary gland of an adult female mammal harboring said hybrid gene in its genome; and
    (ii) said expression system comprises a genomic DNA molecule encoding biologically functional human BSSL/CEL operatively linked to a promoter of a gene that is expressed in the mammary gland of a mammal;

(b) introducing the fertilized egg containing the expression system into a host non-human mammal of the same species as the fertilized egg;

(c) allowing the host non-human mammal to produce progeny; and (d) selecting a female progeny non-human mammal that expresses recoverable amounts of biologically functional human BSSL/CEL in its milk.

2. A transgenic non-human female mammal that contains an expression system in its genome wherein said expression system comprises a genomic DNA molecule encoding biologically functional human BSSL/CEL operatively linked to a promoter of a gene where in said transgenic mammal expresses recoverable amounts of biologically functional human BSSL/CEL in its milk.

3. A transgenic non-human female mammal according to claim 2 wherein said expression system comprises the DNA of SEQ ID. NO. 1.

4. A method for the production of milk containing biologically functional human BSSL/CEL from a transgenic non-human mammal, comprising:

(a) preparing a female non-human mammal that expresses recoverable amounts of biologically functional human BSSL/CEL in its milk according to the method of claim 1; and (b) milking said mammal.

* * * * *

UNITED STATES PATENT AND TRADEMARK OFFICE
CERTIFICATE OF CORRECTION

PATENT NO. : 5,716,817
DATED : February 10, 1998
INVENTOR(S) : Tornell

It is certified that error appears in the above-indentified patent and that said Letters Patent is hereby corrected as shown below:

On the title page, item[19]:

Delete "Tornell" as the name of the inventors, and insert therefor -- Hansson et al. --.

After "[75] Inventors:" insert -- Stig Lennart Hansson, Umea, Sweden; --.

Signed and Sealed this

Twenty-second Day of June, 1999

Attest:

Q. TODD DICKINSON

Attesting Officer

Acting Commissioner of Patents and Trademarks